(12) United States Patent
Lin et al.

(10) Patent No.: US 6,861,053 B1
(45) Date of Patent: Mar. 1, 2005

(54) METHODS OF DIAGNOSING OR TREATING IRRITABLE BOWEL SYNDROME AND OTHER DISORDERS CAUSED BY SMALL INTESTINAL BACTERIAL OVERGROWTH

(75) Inventors: Henry C. Lin, Manhattan Beach, CA (US); Mark Pimentel, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/374,142

(22) Filed: Aug. 11, 1999

(51) Int. Cl.$^7$ ................. A01N 63/00; A01N 65/00; A01N 37/18; A61K 35/00; A61K 39/00

(52) U.S. Cl. ............... 424/93.1; 424/93.4; 424/93.45; 424/114; 424/116; 424/184.1; 514/2

(58) Field of Search ................ 424/93.1, 93.4, 424/93.45, 114, 116, 184.1; 514/2, 192, 198; 435/32, 4

(56) References Cited

U.S. PATENT DOCUMENTS

| | | |
|---|---|---|
| 4,673,680 A | 6/1987 | Pendleton |
| 4,970,207 A | 11/1990 | Sato et al. |
| 5,041,431 A | 8/1991 | Halskov |
| 5,120,306 A | 6/1992 | Gosselin |
| 5,219,871 A | 6/1993 | Cross et al. |
| 5,225,352 A | 7/1993 | Zanetta et al. |
| 5,236,901 A | 8/1993 | Burks et al. |
| 5,380,522 A | 1/1995 | Day |
| 5,426,028 A | 6/1995 | Levy et al. |
| 5,434,174 A | 7/1995 | Gidda et al. |
| 5,443,826 A | 8/1995 | Borody |
| 5,453,428 A | 9/1995 | Kaminski |
| 5,519,014 A | 5/1996 | Borody |
| 5,538,856 A | 7/1996 | Levy et al. |
| 5,547,961 A | 8/1996 | Ohta et al. |
| 5,550,132 A | 8/1996 | Benson et al. |
| 5,589,168 A | 12/1996 | Allen et al. |
| 5,599,795 A * | 2/1997 | McCann et al. |
| 5,612,366 A | 3/1997 | Becker et al. |
| 5,627,200 A | 5/1997 | Kreutter et al. |
| 5,645,997 A | 7/1997 | Kline et al. |
| 5,648,355 A | 7/1997 | Theoharides |
| 5,648,359 A | 7/1997 | Ohashi et al. |
| 5,660,828 A | 8/1997 | Rodriguez et al. |
| 5,668,143 A | 9/1997 | Ku et al. |
| 5,677,326 A | 10/1997 | Tsuchiya et al. |
| 5,679,684 A | 10/1997 | Benson et al. |
| 5,684,017 A | 11/1997 | Harrison et al. |
| 5,691,343 A * | 11/1997 | Sandborn et al. |
| 5,703,100 A | 12/1997 | McDonald et al. |
| 5,707,642 A | 1/1998 | Yue |
| 5,726,187 A | 3/1998 | Gaster et al. |
| 5,728,380 A | 3/1998 | Allen et al. |
| 5,736,560 A | 4/1998 | Cosford et al. |
| 5,753,218 A | 5/1998 | Smith et al. |
| 5,759,546 A | 6/1998 | Weinberg et al. |
| 5,780,026 A | 7/1998 | Yoshii et al. |
| 5,821,259 A | 10/1998 | Theoharides |
| 5,830,668 A | 11/1998 | Mordechai et al. |
| 5,833,987 A | 11/1998 | Noelle et al. |
| 5,834,215 A | 11/1998 | Garry et al. |
| 5,846,933 A | 12/1998 | Korngold et al. |
| 5,852,041 A | 12/1998 | Cosford et al. |
| 5,858,403 A | 1/1999 | Borody et al. |
| 5,863,529 A | 1/1999 | Rodriguez |
| 5,869,262 A | 2/1999 | Gallatin et al. |
| 2002/0018809 A1 * | 2/2002 | Stoll .................... 424/464 |
| 2003/0050308 A1 * | 3/2003 | Brunner et al. ........... 514/224.2 |
| 2003/0124566 A1 * | 7/2003 | Kong et al. .................. 435/6 |
| 2003/0152919 A1 * | 8/2003 | Roelens et al. ............... 435/6 |
| 2003/0185754 A1 * | 10/2003 | Cohen et al. ............... 424/9.2 |
| 2003/0215421 A1 * | 11/2003 | McDonald et al. ........ 424/85.1 |

OTHER PUBLICATIONS

Weilman et al (Klin Wochenstr vol. 60 No. 7, pp 371–374), 1982.

Friedman (Gastroenterology Clinics of N. America vol. 20, No. 2, pp 313–324), 1991.

Way et al (Current Surgical Diagnosis & Treatment, 9$^{th}$ Ed. p. 1083), 1991.*

Annese, V. et al.., *Gastrointestinal motility disorders in patients with inactive Crohn's disease*, Scand J Gastroenterol, 32(11):1107–17 (Nov. 1997). Abstract Only.

Autschbach, F. et al., *In situ expression of interleukin–10 in noninflamed human gut and in inflammatory bowel disease*, Am J Pathol, 153(1):121–30 (Jul. 1998). Abstract Only.

Alander, M. et al., *The effect of probiotic strains on the microbiota of the Simulator of the Human Intestinal Microbial Ecosystem (SHIME)*, Int J Food Microbiol, 46(1):71–9 (Jan. 12, 1999). Abstract Only.

(List continued on next page.)

*Primary Examiner*—Mark Navarro
(74) *Attorney, Agent, or Firm*—Pillsbury Winthrop LLP

(57) ABSTRACT

Disclosed is a method of diagnosing irritable bowel syndrome, fibromyalgia, chronic fatigue syndrome, depression, attention deficit/hyperactivity disorder, autoimmune diseases, such as multiple sclerosis and systemic lupus erythematosus, or Crohn's disease, which involves detecting the presence of small intestinal bacterial overgrowth (SIBO) in a human subject having at least one symptom associated with a suspected diagnosis of any of those diagnostic categories. Also disclosed is a method of treating these disorders, and other disorders caused by SIBO, that involves at least partially eradicating a SIBO condition in the human subject. The method includes administration of antimicrobial or probiotic agents, or normalizing intestinal motility by employing a prokinetic agent. The method improves symptoms, including hyperalgesia related to SIBO and disorders caused by SIBO. Also disclosed is a kit for the diagnosis or treatment of irritable bowel syndrome, fibromyalgia, chronic fatigue syndrome, depression, attention deficit/hyperactivity disorder, autoimmune diseases, or Crohn's disease.

31 Claims, 3 Drawing Sheets

OTHER PUBLICATIONS

Alpert, J.E. et al., *Attention deficit hyperactivity disorder in childhood among adults with major depression*, Psychiatry Res, 62(3):213–9 (Jun. 1, 1999). Abstract Only.

Babyatsky, M.W. et al., *Expression of transforming growth factors alpha and beta in colonic mucosa in inflammatory bowel disease*, Gastroenterology, 110(4):975–84 (Apr. 1996). Abstract Only.

Bell, Iris R. et al., *Illness from Low Levels of Enviromental Chemicals: Relevance to Chronic Fatigue Syndrome and Fibromyalgia*, The American Journal of Medicine, vol. 105 (3A), pp. 74S–82S (Sep. 28, 1998).

Bennett, G. et al., *Nerve growth factor induced hyperalgesia in the rat hind paw is dependent on circulating neutrophils*, Pain, 77:315–322 (1998).

Bjornsson, E. S., *comparison between physiologic and erythromycin–induced interdigestive motility*, Scand J. Gastroenterol, 30(2):139–45 (Feb. 1995). Abstract Only.

Bruin, K. F. et al., *Modulation of cytokine release from human monocytes by drugs used in the therapy of inflammatory bowel diseases*, Eur J. Gastroenterol Hepatol, 7(8):791–5 (Aug. 1995). Abstract Only.

Bruno, Richard L. et al., *Parallels Between Post–Polio Fatigue and Chronic Fatigue Syndrome: A Common Pathophysiology?*, The American Journal of Medicine, 105(3A):66A–73S (1998).

Camoglio, L. et al., *Altered expression of interferon–gamma and interleukin–4 in inflammatory bowel disease*, Inlfamm Bowel Dis, 4(4):285–90 (Nov. 1998). Abstract Only.

Casafont, Morencos F. et al., *Small bowel bactrial overgrowth in patinets with alcholic cirrhosis*, Dig Dis Sci, 41(3):552–6 (Mar. 1996). Abstract Only.

Casini–Raggi, V. et al., *Mucosal imbalance of IL–1 and IL–1 receptor antagonist in inflammatory bowel disease. A novel mechanism of chronic intestinal inflamation*, J Immunol, 154(5):2434–40 (Mar. 1, 1995). Abstract Only.

Castedal M., *Postprandial peristalsis in the human duodenum*, Neurogastroenterol Motil, 10(3):227–33 (Jun. 1998). Abstract Only.

Chang C. S., et al., *Small intestine dysmotility and bacterial overgrowth in cirrhotic patinets with spontaneous bacterial peritonitis*, Hepatology, 28(5):1187–90 (Nov. 1998). Abstract Only.

Chang, C. S., *Increased accuracy of the carbon–14 D–xylose breath test in detecting small–intestinal bacterial overgrowth by correction with the gastric emptying rate*, Eur J Nucl Med, 22 (10):1118–22 (Oct. 1995), Abstract Only.

Chesta, J., *Abnormalities in proximal small bowel motility in patients with cirrhosis*, Hepatology, 17(5):828–32 (May 1993). Abstract Only.

Cominelli, F., *Interleukin–1 and interleukin–1 receptor antagonist in inflammatory bowel disease*, Aliment Pharmacol Ther, 10 Suppl 2:49–53; discussion 54 (1996). Abstract Only.

Corazza, G. R., *The diagnosis of small bowel bacterial overgrowth. Reliability of jejunal culture and inadequacy of breath hydrogen testing*, Gastroenterology, 98(2):302–9 (Feb 1990). Abstract Only.

Corazza, G., *Prevalence and consistency of low breath H2 excretion following lactulose ingestion. Possible implications for the clinical use of the H2 breath test* Dig dis Sci 38(11):2010–6 (Nov. 1993). Abstract Only.

Daig, R. et al., *Increased interleukin 8 expression in colon mucosa of patients with inflammatory bowel disease*, Gut, 38(2):216–22 (Feb 1996). Abstract Only.

Dantzer, Robert et al., *Cytokines and Sickness Behavior*, Annals New York Academy of Sciences, vol. 840, pp. 586–590 (May 1, 1998).

De Becker, Pascale, et al., *Autonomic Testing in Patients with Chronic Fatigue Syndrome*, The American Journal of Medicine, vol. 105(3A), pp. 22S–26S (Sep. 28, 1998).

de Boissieu, D., et al., *Small–bowel bacterial overgrowth in children with chronic diarrhea, abdominal pain, or both*, The Journal of Pediatrics, vol. 128, No. 2, pp. 203–207 (Feb. 1996).

de Campos, R. O. P. et al., *Systemic treatment with Mycobacterium bovis bacillus calmette–guérin (BCG) potentiates kinin B, receptor agaonist–induced nociception and oedeme formation in the formalin test in mice*, Neuropeptides, vol. 32 No. 5, pp. 393–403 (1998).

Dellert, S. F. et al., *the 13C–xylose breath test for the diagnosis of small bowel bacterial overgrowth in children*, J Pediatr Gastoenterol Nutr, 25(2):153–8 (Aug. 1997) Abstract Only.

Demitrack, Mark A., *Neuroendocrine Aspects of Chronic Fatigue syndrome: A Commentary*, The American Journal of Medicine, vol. 105 (3A), pp. 11S–14S (Sep. 28, 1998).

Dinarello, C.A., *role of pro– and anti–inflammatory cytokines during inflammation: experimental and clinical findings*, J Biol Regul Homeost Agent, 11(3):91–103 (Jul.–Sep. 1997. Abstract Only.

Evans, P. R. et al.., *Gastroparesis and small bowel dysmotility in irritable bowel syndrome*, Dig Dis Sci, 42(10):2087–93 (Oct. 1997). Abstract Only.

Faraone, S. V. et al., *Psychiatric, neuropsychological, and psychosocial feature of DSM–IV subtypes of attention–deficit/hyperactivity disorder: results from a clinically referred sample*, J Am Acad Child Adolesc Psychiatry, 37(2):185–93 (Feb 1998). Abstract Only.

Feghali, C. A et al., *Cytokines in acute and chronic inflammantion*, Front Biosci, 2:d12–26 (Jan. 1997). Abstract Only.

Feher, E. et al., *Direct morphological evidence of neuroimmunomoudulation in colonic mucosa of patients with Crohn's disease*, Neuroimmunomodulation, 4(5–6):250–7 (Sep.–Dec. 1997). Abstract Only.

Fellermann, K. et al., *Steroid–unresponsive acute attacks of inflammatory bowel disease: immunomodulation by tacrolimus (FK506)*, Am J Gastroenterol, 93(10):1860–6 (Oct. 1998). Abstract Only.

Fenner, H., [*No tittle available*], Zheumatol, 57(5):294–7 (Oct. 1998). Abstract Only.

Funakoshi, K. et al., *spectrum of cytokine gene expression in intestinal mucosal lesions of Crohn's disease and ulcerative colitis*, Digestion, 59(1):73–8 (1998). Abstract Only.

Gardiner, G et al., *Development of a Probiotic Cheddar Cheese Containing Human–Derived Lactobacillus paracasei Strains*, Applied and Environmental Microbiology, vol. 64, No. 6, pp. 2192–99 (1998).

Gielkens, H. A. et al., *Interdigestive antroduodenal motility and gastric acid secretion*, Aliment Pharmacol Ther, 12(1):27–33 (Jan. 1998). Abstract Only.

Glaser, Ronald, *Stress–Associated Immune Modulation: Relevance to Viral Infections and Chronic Fatigue Syndrome*, The American Journal of Medicine, vol. 105 (3A), pp. 35S–42S (Sep. 28, 1998).

Gorard, D.A, et al., *Ambulatory small intestinal motility in 'diarrhoea' predominant irritable bowel syndrome, Gut*, 35(2):203–10 (1994). Abstract Only.

Gorard, D. A. et al., *Intestinal motor function in irritable bowel syndrome, Dig Dis*, 12(2):72–84 (Mar.–Apr. 1994). Abstract Only.

Guimbaud, R et al., *Network of inflammatory cytokines and correlation with disease activity in ulcerative colitis, Am J. Gastroenterol*, 93(12):2397–404 (Dec. 1998). Abstract Only.

Hang, L. et al., *Cytokine repertoire of epithelial cells lining the human urinary tract, J Urol* 159(6):2185–92 (Jun. 1998). Abstract Only.

Harlow, Bernard L, *Reproductive Correlates of Chronic Fatigue Syndrome, The American Journal of Medicine*, vol. 105(3A), pp. 94S–99S (Sep. 28, 1998).

Hellstrom, P.M. et al., *Role of bile in regulation of gut motility, J Intern Med* 237(4):395–402 (Apr. 1995). Abstract Only.

Hori, T et al., *Pain Modulatory Actions of Cytokines and Prostaglandin $E_2$ in the Brain*, Annals New York Academy of Sciences, vol. 840, pp. 269–281 (May 1, 1998).

Hudziak; J. J. et al., *Latent class and factor analysis of DSM–IV ADHD: a twin study of female adolescents, J Am Acad Child Adolesc Psychiatry*, 37(8):848–57 (Aug. 1998). Abstract Only.

Hyams, J. S. et al., *Relationship of interleukin–1 receptor antagonist to mucosal inflmmation in inflammatory bowel disease, J Pediatr Gastroenterol Nutr*, 21(4):419–25 (Nov. 1995). Abstract Only.

Jason, Leonard et al., *Estimating the Prevalence of Chronic Fatigue Syndrome Among Nurses, The American Journal of Medicine*, vol. 105 (3A), pp. 91–93S (Sep. 28, 1998).

Kanik, K.S. et al., *Distinct patterns of cytokine secretion characterize new onset synovitis versus chronic rheumatoid arthritis, J. Rheumatol*, 25(1):16–22 (Jan. 1998). Abstract Only.

Kellow, J. E. et al., *Enhanced perception of physiological intestinal motility in the irritable bowel syndrome, Gastroenterology*, 101(6):1621–7 (Dec. 1991). Abstract Only.

Kerlin, P. et al., *Breath hydrogen testing in bactgerial overgrowth of the small intestine, Gastroenterology*, 95(4):982–8 (Oct 1988). Abstract Only.

King, C. E. et al., *Comparison of the 1–gram [14C]xylose, 10–gram lactulose–H2, and 80–gram glucose–H2 breath test in patients with small intestine bacterial overgrowth, Gastroenterology*, 91(6):1447–51 (Dec. 1996). Abstract Only.

Kontula, P. et al., *The effect of lactose derivatives on intestinal lactic acid bacteria, J Dairy Sci* 82(2):249–56 (Feb. 1999). Abstract Only.

Kuboyama, S., *Increased circulating levels of interleukin–1 receptor antagonist in patients with inflmmatory bowel disease Kurume Med J.* 45(1):33–7 (1998). Abstract Only.

Kucharzik, T., *Circulating antiflammatory cytokine IL–10 in patients with inflammatory bowel disease (IBD), Clin Exp Immunol*, 100(3):452–6 (Jun. 1995). Abstract Only.

Kucharzik, T. et al, *Immunoregulatory profperties of IL–13 in patinets with inflammatory bowel disease; comparison with IL–4 and IL–10 Clin Exp Immunol*, 104(3):483–90 (Jun 1996). Abstract Only.

Kucharzik, T., *Synergistic effect of immunoregulatory cytokines on peripheral blood monocytes from patients with inflammatory bowel disease, Dig Dis Sci*, 42(4):805–12 (Apr. 1997). Abstract Only.

LaManca, John J., *Influence of Exhaustive Treadmill Exercise on Congnitive Functioning in Chronic Fatigue Syndrome, The American Journal of Medicine*, vol. 105 (3A), pp. 59S–65S (Sep. 28, 1998).

Lange, Gudrun et al., *Neuroimaging in Chronic Fatigue Syndrome, The American Journal of Medicine*, (vol. 105 (3A), pp. 50S–53S (Sep. 28, 1998).

Leiper, K. et al., *Adjuvant post–operative therapy, Baillieres Clin Gastroenterol*, 12(1):179–99 (Mar. 1998). Abstract Only.

Lembckem, B., *[Breath test in intestinal diseases and functional gastrointestinal diagnosis], Schweiz Rundsch Med Prax*, 86(25–26):1060–7 (Jun. 18, 1997). Abstract Only.

Levine, Paul H., *What We Know About Chronic Fatigue Syndrome and Its Relevance to the Practicing Physician, The American Journal of Medicine*, vol. 105(3A), pp. 100S–103S (Sep. 28, 1998).

Lewindon, P. J. et al., *Bowel dysfunction in cystic fibrosis: importance of breath test, J Paediatr Child Health*, 34(1):79–82 (Feb. 1998), Abstract Only.

Lugering, N. et al., *Current concept of the role of monocytes/macrophages in inflammatory bowel disease–balance of proinflnmatory and immunosupressive mediators, Ital J Gastroenterol Hepatol*, 30(3):338–44 (Jun. 1998). Abstract Only.

Luiking, Y. C. et al., *Migrating motor complex cycle duration is determined by gastric or duodenal origin of phase III, Am J Physiol*, 275(6 Pt 1):G1246–G1251 (Dec. 1998). Abstract Only.

MacDermott, R. P., *Alterations of the mucosal immune system in inflammatory bowel disease, J Gastroenterol*, 31(6):907–16 (Dec. 1996).

Marlin, Richard G., *An Evaluation of Multidisciplinary Intervention for Chronic Fatigue syndrome with Long–Term Follow–Up, and a Comparison with Untreated Controls, The American Journal of Medicine*, vol. 105(3A), pp. 110S–114S (Sep. 28, 1998).

Mack, D. R. et al., *Small bowel bacterial overgrowth as a cause of chronic diarrhea after liver transplantation in children, Liver Traspl Surg*, 4(2):166–9 (Mar. 1998). Abstract Only.

Maini, R. N., *A perspective on anti–cytokine and anti–T cell–directed therapies in rheumatoid arthritis, Clin Exp Rheumatol*, 13 Suppl 12:S35–40 (Sep.–Oct. 1995). Abstract Only.

Mastropaolo, G. et al., *Evaluation of the hydrogen breath test in man: difinition and elimination of the early hydrogen peak, Gut*, 28(6):721–5 (Jun. 1987). Abstract Only.

Matsukawa, A., *Analysis of the inflmmatory cytokine network among TNF alpha, IL–1 beta, IL–1 receptor antagonist, and IL–8 in LPS–induced rabbit arthritis Lab Invest*, 76(5):629–38 (May 1997). Abstract Only.

Matsukawa, A. et al., *Sequential generation of cytokines during the initiative phase of inflammation, with reference to neutrophils, Inflamm Res*, 47 Suppl 3:S137–44 (Oct. 1998). Abstract Only.

Morencos, F. Casafont et al., Small Bowel Bacterial Overgrowth in Patients with Alcoholic Cirrhosis, *Digestive Diseases and Sciences*, vol. 40, No. 6 (Jun. 1995).

Muller, S. et al., *Activated CD4+ and CD8+ cytotoxin cells are present in increased numbers in the intestinal mucosa from patients with active inflammatory bowel disease, Am J Pathol*, 152(1):261–8 (Jan. 1998), Abstract Only.

Murata, Y., *The role of proinflmmatory and immunoregulatory cytokines in the pathogenesis of ulcerative coilitis, J. Gastroenterol*, 30 Suppl 8: 56–60, (Nov. 1995). Abstract Only.

Murphy, K., *Adults with attention deficit hyperactivity disorder: assessment and treatment considerations, Semin Speech Lang*, 17(3):245–53; quiz 254 (Aug. 1996). Abstract Only.

McVay, L. D., Changes in human mucosal gamma delta T cell repertoire and function associated with the disease process in inflammatory bowel disease, *Mol Med*, 3(3):183–203 (Mar. 1997). Abstract Only.

Naidu, A. S et al., *Probiotic spectra of lactic acid bacteria (LAB), Crit Rev Food Sci Nutr*, 39(1):13–126 (Jan. 1999). Abstract Only.

Nassif, A. et al., *Role of cytokines and plantelet–activating factor in inflammatory bowel disease. Implications for therapy., Dis Colon Rectum*, 39(2):217–23 (Feb. 1996). Abstract Only.

Natelson, Benjamin H., *Immunologic Parameters in Chronic Fatigue Syndrome, Major Depression, and Multiple Sclerosis, The American Journal of Medicine*, vol. 105 (3A), pp. 43S–49S (Sep. 28, 1998).

Nielsen, O. H., *Intestinal interleukin–8 concentration and gene expession in inflammatory bowel disease, Scand J Gastroenterol*, 32(10):1028–34 (Oct. 1997), Abstract Only.

Niessner, M., *Altered Th1/Th2 cytokine profiles in the intesinal mucosa of patients with inflammatory bowel disease as assessed by quantitative reversed transcribed polymerase chain reaction (RT–PCR), Clin Exp Immunol*, 101(3):428–35 (Sep. 1995). Abstract Only.

Nieuwenhuijs, V. B. et al., *Disrupted bile flow affects interdigestive small bowel motility in rats, Surgery*, 122(3):600–8 (Sep. 1997). Abstract Only.

Nieuwenhuijs, V.B. et al., *The role of interdigestive small bowel motility in the regulation of gut microflora, bacterial overgrowth, and bacterial translocation in rats, Ann Surg*, 22B:(2):188–93 (Aug. 1998), Abstract Only.

Nieuwenhuijs, V. B. et al., *The effects of ABT–229 and octreotide on interdigestive small bowel motility, bacterial overgrowth and bacterial translocation in rats, Eur J Clin Invest*, 29(1):33–40 (Jan. 1999). Abstract Only.

Panja, A, et al., *The regulation and functional consequence of proinflammatory cytokine binding on human intestinal epithelial cells, J Immunol*, 161(7):3675–84 (Oct. 1998). Abstract Only.

Parkes, M. et al., *Contribution of the IL–2 and IL–10 genes to inflammatory bowel disease (IBD) susceptibility, Clin Exp Immunol* 113(1):28–32 (Jul. 1998). Abstract Only.

Peterson, R. L. et al., *Molecular effects of recombinant human interleukin–11 in the HLA–B27 rat model of inflammatory bowel disease, Lab Invest*, 78(12):1503–12 (Dec. 1998). Abstract Only.

Poole, S, et al., *Bradykinin B1 and B2 receptors, tumor necrosis factor alpha and inflammatory hyperalgesia, Br J Pharmacol*, 126(3):649–56 (Feb. 1999). Abstract Only.

Propst, A. et al., *Interleukin–1 receptor antagonist in differential diagnosis of inflammatory bowel diseases, Eur J Gastroenterol Hepatol*, 7(11):1031–6 (Nov. 1995). Abstract Only.

Radford–Smith, G., *Cytokines and inflammatory bowel disease, Baillieres Clin Gastroenterol*, 10(1):151–64 (Mar. 1996). Abstract Only.

Reimund, J. M. et al., *Antioxidants inhibit the in vitro production of inflammatory cytokines in Crohn's disease and ulcerative colitis, Eur J Clin Invest*, 28 (2):145–50 (Feb 1998). Abstract Only.

Rhodes, J. M. et al., *The lactulose hydrogen breath test as a diagnostic test for small–bowel bacterial overgrowth, Scand J Gastroenterol* 14(3):333–6 (1979). Abstract Only.

Riordan, Stephen M. et al., *Small Intestinal Bacterial Overgrowth in the Symptomatic Elderly, The American Journal of Gastroenterology*, vol. 92, No. 1, pp. 47–51, (1997).

Riordan, S. M. et al., *The lactulose breath hydrogen test and small intestinal bacterial overgrowth, Am J Gastroenterol*, 91(9):1795–803 (Sep. 1996). Abstract Only.

Rogler, G. et al., *Cytokines in inflammatory bowel disease, World J Surg*, 22(4):382–9 (Apr. 1998). Abstract Only.

Rowe, Peter C., et al., *Neurally Mediated Hypotension and Chronic Fatigue syndrome, The American Journal of Medicine*, vol. 105 (3A), pp. 15S–21S (Sep. 28, 1998).

Ruseler–van Embden, J. G., et al., *Anaerobic gram–negative faecal flora in patients with Crohn's disease and healty subjects, Antonie Van Leeuwenhock*, 49(2):125–32 (Jun. 1983). Abstract Only.

Saiki, T. et al., *Detection of pro– and anti–inflammatory cytokines in stools of patients with inflammatory bowel disease, Scand J Gastroenterol*, 33(6):616–22 (Jun. 1998). Abstract only.

Sakai, T. et al., *Interleukin 15 activity in the rectal mucosa of inflammatory bowel disease, Gastroenterology*, 114(6):1237–43 (Jun. 1998). Abstract Only.

Sartor, R. Balfour, *Pathogenesis and Immune Mechanisms of Chronic Imflammatory Bowel Disease, The American Journal of Gastroenterology*, vol. 92, No. 12, pp. 5S–11S (1997).

Schmidt, T. et al., *Ambulatory 24–hour jejuanl motility in diarrhea–predominant irritable bowel syndrome, Scand J Gastroenterol*, 31(6):581–9 (Jun. 1996). Abstract Only.

Schneider, A. et al., *Value of the 14C–D–xylose breath test in patients with intestinal bacterial overgrowth, Digestion*, 32(2):86–91 (1985). Abstract Only.

Schreiber, S. et al., *Impaired response of activated mononuclear phagocytes to interleukin 4 in inflammatory bowel disease, Gastroeneterology*, 108(1):21–33 (Jan. 1995). Abstract Only.

Schreiber, S. et al., *Immunoregulatory role of interleukin 10 in patients with inflammatory bowel disease, Gastroenterology*, 108(5):1434–44 (May 1995). Abstract Only.

Schreiber, S., *Experimental immunomodulatory therapy of inflammatory bowel disease, Neth J Med*, 53(6):S24–31 (Dec. 1998). Abstract Only.

Sharpe, Michael, *Cognitive Behavior Therapy for Chronic Fatigue Syndrome: Efficacy and Implications, The American Journal of Medicine*, vol. 105 (3A), pp. 104S–109S (Sep. 28, 1998).

Shigematsu, S., *Therepeutic potential of interleukin–1 receptor antagonist in inflammatory bowel disease, Kurume Med J.*, 45(2):175–9 (1998). Abstract Only.

Soderholm, Johan D. et al., *Epithelial Permeability to Protein in the Noninflamed ileum of Crohn's Disease, Gastroenterology*, vol. 117, pp. 65–72, (1999).

Spanhaak, S., *The effect of consumption of milk fermented by Lactobacillus casei strain Shirota on the intestinal microflora and immune paramenters in humans*, Eur J Clin Nutr, 52(12):899–907 (Dec. 1998). Abstract Only.

Stack, W. A. et al., *Randomised controlled trial of CDP571 antibody to tumour necrosis factor–alpha in Crohn's disease*, Lancet, 349(9051):521–4 (Feb. 22, 1997). Abstract Only.

Stotzer, P. O. et al., *Interdigestive and postprandial motility in small–intestinal bacterial overgrowth*, Scand J Gastroenterol, 31(9):875–80 (Sep. 1996). Abstract Only.

Strocchi, A et al., *Detection of malabsorption of low doses of carbohydrate accuracy of various breath H2 criteria*, Gastroenterology 105(5):1404–10 (Nov. 1993). Abstract Only.

Swanink, C. M. et al., *Yersinia enterocolitica and the chronic fatigue syndrome*, J Infect, 36(3):269–72 (May 1998). Abstract Only.

Swart, G. R. et al., *13C breath test in gastroenterological practice Scand J. Gastroenterol Suppl*, 225:13–8 (1998). Abstract Only.

Steele, Lea et al., *The Epidemiology of Chronic Fatigue in San Francisco*, The American Journal of Medicine, vol. 105 (3A), pp. 83S–90S (Sep. 28, 1998).

Shirachi, A., *Therapeutic implications of interleukin–10 in inflammatory bowel disease*, Kurume Med J, 45(1):63–7 (1998). Abstract Only.

Targan, Stephen R. et al., *A short–term study of chimeric monoclonal antibody cA2 to tumor necrosis factor alpha for Crohn's disease*, The New England Journal of Medicine, vol. 337, No. 15, pp. 1029–35 (Oct. 9, 1997).

Targan, Stephen R. et al., *The Utility of ANCA and ASCA in Inflammatory Bowel Disease*, Inflammatory Bowel Disease, vol. 5, No. 1, pp. 61–3 (Feb. 1999).

Terman, Michael et al., *Chronic Fatigue syndrome and Seasonal Affective disorder: Comorbidity, diagnostic Overlap, and Implications for Treatment*, The American Journal of Medicine, vol. 105 (3A), pp. 115S–124S ((Sep. 28, 1998).

Tirelli, Umberto et al., *Brain Positron Emisson Tomography (PET) in Chronic Fatigue Syndrome: Preliminary Data*, The American Journal of Medicine, vol. 105 (3A), pp. 54S–58S (Sep. 28, 1998).

Triadafilopoulos, George et al., *Digestive Diseases and Sciences*, Vo. 36, No. 1, pp. 59–64 (Jan. 1991).

van den Berg, W. B. *Joint inflammation and cartilage destruction may occur uncoupled*, Springer Semin Immunopathol, 20(1–2):149–64 (1998). Abstract Only.

Vanderhoof, J. A. et al., *Treatment strategies for small bowel bacterial overgrowth in short bowel syndrome*, J Pediatr Gastroenterol Nutr, 27(2):155–60 (Aug. 1998). Abstract Only.

Vanderhoof, J. A. et al., *Use of probiotics in childhoon gastrointestinal disorders*, J Pediatr Gastroenterol Nutr 27(3):323–32 (Sep. 1998). Abstract Only.

van Dullemen, H. M. et al., *Treatment of Crohn's disease with anti–tumor necrosis factor chimeric monoclonal antibody (cA2)*, Gastroenterology, 109(1):129–35 (Jul. 1995). Abstract Only.

van Hogezand, R. A. et al., *Selective Immunomodulation in patients with inflammatory bowel disease–future therapy or reality?*, Neth J Med, 48(2):64–7 (Feb 1996). Abstract Only.

van Hogezand, R. A. et al., *The future role of anti–tumour necrosis factor–apha products in the treatment of Crohn's disease*, Drugs, 56(3):299–305 (Sep. 1998). Abstract Only.

Varni, James W. et al., *Chronic Pain and Emotional Distress in Children and Adolescents*, Dev. Behav. Ped., vol. 17, No. 3, pp. 154–161 (Jun. 1996).

Verkijk, M. et al., *Effect of gastrin on antroduodenal motility: role of intraluminal acidity*, Am J Physiol, 275(5 PT 1):G1209–16. Abstract Only.

Weckmann, A. L. et al., *Cytokine inhibitors in autoimmune disease*, Semin Arthritis Rheum, 26(2):539–57 (Oct. 1996). Abstract Only.

Wolf, B. W. et al., *Safety and tolerance of Lactobacillus reuteri supplementation to a population infected with the human immunodeficiency virus*, Food Chem Toxicol, 36(12):1085–94 (Dec. 1998). Abstract Only.

Wolfe, Frederick et al., *Aspects of Fibromyalgia in the General Population: Sex, Pain Thresholdm and Fibromyalgia Symptoms*, The Journal of Rheumatology, vol. 22, pp. 151–6 (1995).

Wolfe, Frederick, *Fibromyalgia: The Clinical Syndrome*, Rheumatic Disease Clinics of North America, vol. 15, No. 1, pp. 1–17 (Feb. 1989).

Woo, P., *Cytokines in juvenile chronic arthritis*, Baillieres Clin Rheumatol, 12(2):219–28 (May 1998). Abstract Only.

Whiteside, Theresa L. et al., *Natural Killer Cells and Natural Killer Cell Activity in chronic Fatigue Syndrome*, The American Journal of Medicine, vol. 105 (3A), pp 27S–34S (Sep. 28, 1998).

XP–000978709 Mark Pimentel, et al. *Eradication Of Small Intestinal Bactewrial Overgrowth Decreases The Gastrointestinal Sympotoms In Fibromyalgia*, Gastroenterology, vol. 118, No. 4 Supl. 2 Part 1, p. AGA A413 (2000–04).

XP–000978710 Mark Pimentel, et al. *Comparsion of Peak Breath Hydrogen Production in Patients with Irritable Bowel Syndrome, Chronic Fatigue Syndrome and Fibromyalgia*, Gastroenterology, vol 118, No. 4 Suppl. 2 Part 1, p. AGA A413 (2000–04).

XP–000979125 Mark Pimentel, et al. *Eradication of Small Intestinal Bacterial Overgrowth Decreases Symoptoms in Chronic Fatigue Syndrome: A Double Blind, Randomized Study*, Gastroenterology, vol. 118, No. 4 Suppl. 2 Part. 1, p. AGA A414 (2000–4) Arthritis & Rheumatism, vol. 42, No. 9 Suppl., p. S343 (1999).

XP–000979873 E. Lederman, et al. *Bacterial Overgrowth in the Neoterminal Ileum After Illeocolonic Resection for Crohn's Disease*, Gastroenterology, vol. 112, No. 4 Suppl., p. A1023 (1997).

XP000979874 P. Rutgeerts, et al. *Small Bowel Bacterial Overgrowth, Ileal Dysfunction and Stool Fat Excretion in Patients with Unoperated Crohn's Disease*, Gastroenterology, vol. 76, No. 5 Part 2, p. 1232 (1979).

XP–000981459 R.E. Cater, II *The Clinical Importance of Hypochlorhydria (A Consequence of Chronic Helicobater Infection):Its Impossible Etiological Role in Mineral Amino Acid Malabsorption, Depression and Other Symptoms*, Medical Hypotheses, vol. 39, No. 4, pp. 375–383 (1992).

XP–000980196 Raymond Karcher, Ph.D., et al *Using a Cutoff of <10ppm for Breath Hydrogen Testing: A Review of Five Years' Experience*, Annals of Clinical and Laboratory Science, vol. 29, No. 1, pp. 1–8 (1999–01).

XP–000980200 Yuji Funayma, et al. *Anti–bacterial Treatment for Postoperative Bacterial Overgrowth in Crohn's Disease*, Gastroenerology, vol. 112, No. 4 Suppl., p. A1444 (1997) SSAT Abstracts.

XP–002159720 G. Galatola et al., *Diagnosis of Bacterial Contamination of the Small Intestine Using the 1 g '14C! Xylose Breath Test in Various Gastrointestinal Diseases, Minerva Gastroenterol. Dietol.*, vol. 37, pp. 169–175, (1991). Abstract Only.

XP–000980123 S. A. Albano et al., *Small Intestinal Bacterial Overgrowth in Systemic Lupus Erythematosus (SLE), Arthritis & Rheumatism*, vol. 42, No. 9 Suppl., p. S305, Abstract 1409a (Nov. 13–14, 1999).

XP–000979785 C. Prantera et al., *An Antibiotic Regimen for the Treatment of Active Crohn's Disease: A Randomized, Controlled Clinical Trial of Metronidazole plus Ciprofloxacin, The American Journal of Gastroenterology*, vol. 91, No. 2, pp. 328–332 (1996).

XP–000979794 F. Casellas et al., *Potential Usefulness of Hydrogen Breath Test with d–Xylose in Clinical Management of Intertinal Malabsorption, Digestion Diseases and Sciences*, vol. 38, No. 2, pp. 321–327 (Feb. 1993).

XP–000981761 A. Schneider et al., *Value of the 14C–D–Xylose Breath Test in Patients with Intestinal Bacterial Overgrowth, Digestion*, 32:86–91 (1985).

XP–000980122 M. Pimentel et al., *Eradication of Small Intestinal Bacterial Overgrowth Decreases Symptoms in Fibromyalgia: A Double Blind Randomized Study, Arthritis & Rheumatism*, vol. 42, No. 9, Suppl., p. S343, Abstract 1632 (Nov. 13–14, 1999).

* cited by examiner

METHODS OF DIAGNOSING OR TREATING IRRITABLE BOWEL SYNDROME AND OTHER DISORDERS CAUSED BY SMALL INTESTINAL BACTERIAL OVERGROWTH

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts. It relates to a method of diagnosing and treating irritable bowel syndrome and other disorders, such as Crohn's disease, chronic fatigue syndrome, fibromyalgia, depression, attention deficit/hyperactivity disorder, multiple sclerosis, systemic lupus erythematosus and other autoimmune diseases in a human subject.

2. Discussion of the Related Art

Irritable bowel syndrome, Crohn's disease, chronic fatigue syndrome, fibromyalgia, depression, attention deficit/hyperactivity disorder, and autoimmune diseases, e.g., multiple sclerosis and systemic lupus erythematosus, are all clinical conditions of unclear etiology.

Irritable bowel syndrome (IBS) is the most common of all gastrointestinal disorders, affecting 11–14% of adults and accounting for more than 50% of all patients with digestive complaints. (G. Triadafilopoulos et al., Bowel dysfunction in fibromyalgia, Digestive Dis. Sci. 36(1):59–64 [1991]; W. G. Thompson, Irritable Bowel syndrome: pathogenesis and management, Lancet 341:1569–72 [1993]). It is thought that only a minority of people with IBS actually seek medical treatment. Patients with IBS present with disparate symptoms, for example, abdominal pain predominantly related to defecation, alternating diarrhea and constipation, abdominal distention, gas, and excessive mucus in the stool.

A number of possible causes for IBS have been proposed, but none has been fully accepted. (W. G. Thompson [1993]). These hypotheses included a fiber-poor Western diet, intestinal motility malfunction, abnormal pain perception, abnormal psychology or behavior, or psychophysiological response to stress.

A high fiber diet increases stool bulk and shortens gut transit time. However the presence of IBS in non-Western countries, such as China and India, and the failure of dietary fiber supplements to treat IBS in double-blind clinical trials are inconsistent with the "fiber hypothesis" for the causation of IBS. (W. Bi-zhen and P. Qi-Ying, Functional bowel disorders in apparently healthy Chinese people, Chin. J. Epidemiol. 9:345–49 [1988]; K. W. Heaton, Role of dietary fibre in irritable bowel syndrome. In: R. W. Read [ed.], Irritable bowel syndrome, Grune and Stratton, London, pp. 203–22 [1985]; W. G. Thompson et al., Functional bowel disorders and functional abdominal pain, Gastroenterol. Int. 5:75–92 [1992]).

Those experiencing chronic IBS pain are often depressed and anxious. Treatment with tricyclic antidepressants has been used to raise the pain threshold of some IBS patients. (W. G. Thompson [1993]). Abreu et al. and Rabinovich et al. taught the use of corticotropin-releasing factor antagonists to relieve stress-related symptoms, including depression and anxiety, in IBS, anorexia nervosa, and other disorders. (M. E. Abreu, Corticotropin-releasing factor antagonism compounds, U.S. Pat. No. 5,063,245; A. K. Rabinovich et al., Benzoperimidine-carboxylic acids and derivatives thereof, U.S. Pat. No. 5,861,398). Becker et al. taught the use of serotonin antagonists to treat depression and anxiety associated with IBS and other conditions. (D. P Becker et al., Meso-azacyclic aromatic acid amides and esters as serotonergic agents, U.S. Pat. No. 5,612,366).

Those with IBS symptoms have not been shown to have a different psychological or psychosocial make-up from the normal population. (W. E. Whitehead et al., Symptoms of psychologic distress associated with irritable bowel syndrome: comparison of community and medical clinic samples, Gastroenterol. 95:709–14 [1988]). But many IBS patients appear to perceive normal intestinal activity as painful. For example, IBS patients experience pain at lower volumes of rectal distention than normal or have a lower than normal threshold for perceiving migrating motor complex phase III activity. (W. E. Whitehead et al., Tolerance for rectosigmoid distension in irritable bowel syndrome, Gastroenterol. 98:1187–92 [1990]; J. E. Kellow et al., Enhanced perception of physiological intestinal motility in the irritable bowel syndrome, Gastroenterol. 101(6):1621–27 [1991]).

Bowel motility in IBS patients differs from normal controls in response to various stimuli such as drugs, hormones, food, and emotional stress. (D. G. Wangel and D. J. Deller, Intestinal motility in man, III: mechanisms of constipation and diarrhea with particular reference to the irritable bowel, Gastroenterol. 48:69–84 [1965]; R. F. Harvey and A. E. Read, Effect of cholecystokinin on colon motility on and symptoms in patients with irritable bowel syndrome, Lancet i:1–3 [1973]; R. M. Valori et at., Effects of different types of stress and "prokinetic drugs" on the control of the fasting motor complex in humans, Gastroenterol. 90:1890–900 [1986]).

Evans et al. and Gorard and Farthing recognized that irritable bowel syndrome is frequently associated with disordered gastro-intestinal motility. (P. R. Evans et al., Gastroparesis and small bowel dysmotility in irritable bowel syndrome, Dig. Dis. Sci. 42(10):2087–93 [1997]; D A. Gorard and M. J. Farthing, Intestinal motor function in irritable bowel syndrome, Dig. Dis. 12(2):72–84 [1994]). Treatment directed to bowel dysmotility in IBS includes the use of serotonin antagonists (D. P Becker et al., Meso-azacyclic aromatic acid amides and esters as serotonergic agents, U.S. Pat. No. 5,612,366; M. Ohta et al., Method of treatment of intestinal diseases, U.S. Pat. No. 5,547,961) and cholecystokinin antagonists (Y. Sato et al., Benzodiazepine derivatives, U.S. Pat. No. 4,970,207; H. Kitajima et al., Thienylazole compound and thienotriazolodiazepine compound, U.S. Pat. No. 5,760,032). But colonic motility index, altered myoelectrical activity in the colon, and small intestinal dysmotility have not proven to be reliable diagnotic tools, because they are not IBS-specific. (W. G. Thompson [1993]).

Because there has been no known underlying cause for IBS, treatment of IBS has been primarily directed to symptoms of pain, constipation or diarrhea symptoms.

For example, administration of the polypeptide hormone relaxin, used to relax the involuntary muscles of the intestines, is a treatment taught to relieve the pain associated with IBS. (S. K. Yue, Method of treating myofascial pain syndrome with relaxin, U.S. Pat. No. 5,863,552).

Borody et al. taught the use of a picosulfate-containing laxative preparation to treat constipation in IBS, small intestinal bacterial overgrowth, and acute or chronic bacterial bowel infections. (T. J. Borody et at., Picosulfate-containing preparation for colonic evacuation, U.S. Pat. No. 5,858,403). Barody also taught the use of an anti-inflammatory agent to treat IBS. (T. J. Barody, Treatment of non-inflammatory and non-infectious bowel disorders, U.S. Pat. No. 5,519,014). In addition, constipation in IBS has been treated with amidinourea compounds. (J. Yelnosky et al., Amidinoureas for treating irritable bowel syndrome, U.S. Pat. Nos. 4,701,457 and 4,611,011).

Kuhla et al. taught the use of triazinone compounds to relieve IBS symptoms of constipation, diarrhea, and abdominal pain. (D. E. Kuhla et al., Triazinones for treating irritable bowel syndrome, U.S. Pat. No. 4,562,188). And Kitazawa et al. taught the use of napthy- and phenyl-sulfonylalkanoic acid compounds to treat IBS symptoms. (M. Kitazawa et al., Naphthysulfonylalkanoic acid compounds and pharmaceutical compositions thereof, U.S. Pat. No. 5,177,069; M. Kitazawa et al., Phenylsulfonylalkanoic acid compounds and pharmaceutical compositions thereof, U.S. Pat. No. 5,145,869). Day taught an IBS treatment involving the administration of an anion-binding polymer and a hydrophilic polymer. (C. E. Day, Method for treatment of irritable bowel syndrome, U.S. Pat. No. 5,380,522). And Borody et al. taught the use of salicylic acid derivatives to treat IBS. (T. J. Borody et al., Treatment of non-inflammatory and non-infectious bowel disorders, U.S. Pat. No. 5,519,014).

A probiotic approach to the treatment of IBS has also been tried. For example, Allen et al. described the use of a strain of *Enterococcus faecium* to alleviate symptoms. (W. D. Allen et al., Probiotic containing *Enterococcus faecium* strain NCIMB 40371, U.S. Pat. No. 5,728,380 and Probiotic, U.S. Pat. No. 5,589,168). Borody taught a method of treating irritable bowel syndrome by at least partial removal of the existing intestinal microflora by lavage and replacement with a new bacterial community introduced by fecal inoculum from a disease-screened human donor or by a composition comprising Bacteroides and Escherichia coli species. (T. J. Borody, Treatment of gastro-intestinal disorders with a fecal composition or a composition of bacteroides and *E. coli*, U.S. Pat. No. 5,443,826).

Fibromyalgia (FM) is a syndrome of intense generalized pain and widespread local tenderness, usually associated with morning stiffness, fatigue, and sleep disturbances. (F. Wolfe, Fibromyalgia: the clinical syndrome, Rheum. Dis. Clin. N. Amer. 15(1): 1–17 [1989]). Fibromyalgia is often associated with IBS (34–50% of FM cases) or other gastrointestinal symptoms, Raynaud's phenomenon, headache, subjective swelling, paresthesias, psychological abnormality or functional disability, sometimes with overlapping symptoms of coexisting arthritis, lower back and cervical disorders, and tendonitis. Fibromyalgia affects 1–5% of the population and is more prevalent among women than men. (G. Triadafilopoulos et al. [1991]).

As in IBS, a diagnosis of FM correlates with a decreased pain threshold among FM patients compared to non-patients. (F. Wolfe et al., Aspects of Fibromyalgia in the General Population: Sex, Pain Threshold, and Fibromyalgia Symptoms, J. Rheumatol. 22:151–56 [1995]). But other conventional laboratory evaluations of FM patients are uniformly normal. (G. Triadafilopoulos et al. [1991]). The symptoms of FM patients are typically treated with anti-inflammatory agents and low dose tricyclic antidepressants. Administration of relaxin for involuntary muscle dysfunction is also a treatment taught to relieve the pain associated with fibromyalgia. (S. K. Yue, Method of treating myofascial pain syndrome with relaxin, U.S. Pat. No. 5,863,552). However, there has been no known cause of FM to which diagnosis and/or treatment could be directed.

Chronic fatigue syndrome (CFS) affects more than a half million Americans. (P. H. Levine, What we know about chronic fatigue syndrome and its relevance to the practicing physician, Am. J. Med. 105(3A):100S–03S [1998]). Chronic fatigue syndrome is characterized by a sudden onset of persistent, debilitating fatigue and energy loss that lasts at least six months and cannot be attributed to other medical or psychiatric conditions; symptoms include headache, cognitive and behavioral impairment, sore throat, pain in lymph nodes and joints, and low grade fever. (M. Terman et al., Chronic Fatigue Syndrome and Seasonal; Affective Disorder: Comorbidity, Diagnostic Overlap, and Implications for Treatment, Am. J. Med. 105(3A):115S–24S [1998]). Depression and related symptoms are also common, including sleep disorders, anxiety, and worsening of premenstrual symptoms or other gynecological complications. (A. L. Komaroff and D. Buchwald, Symptoms and signs of chronic fatigue syndrome, Rev. Infect. Dis. 13:S8–S11 [1991]; B. L. Harlow et al., Reproductive correlates of chronic fatigue syndrome, Am. J. Med. 105(3A):94S–99S [1998]).

Other physiologic abnormalities are also associated with CFS in many patients, including neurally-mediated hypotension, hypocortisolism, and immunologic dysregulation. (P. H. Levine [1998]). A subgroup of CFS patients complain of exacerbated mood state, diminished ability to work and difficulty awakening during winter months, reminiscent of seasonal affective disorder. (M. Terman et al. [1998]).

The etiology of CFS has been unknown, and the heterogeneity of CFS symptoms has precluded the use of any particular diagnostic laboratory test. (P. H. Levine [1998]). Symptomatic parallels have been suggested between CFS and a number of other disease conditions, resulting from viral infection, toxic exposure, orthostatic hypotension, and stress, but none of these has been shown to have a causal role in CFS. (E.g., I. R. Bell et al., Illness from low levels of environmental chemicals: relevance to chronic fatigue syndrome and fibromyalgia, Am. J. Med. 105(3A):74S–82S [1998]; R. L. Bruno et al., Parallels between post-polio fatigue and chronic fatigue syndrome: a common pathophysiology?, Am. J. Med. 105(3A):66S–73S [1998]; R. Glaser and J. K. Kiecolt-Glaser, Stress-associated immune modulation: relevance to viral infections and chronic fatigue syndrome, Am. J. Med. 105(3A)35S–42S [1998]; P. C. Rowe and H. Calkins, Neurally mediated hypotension and chronic fatigue syndrome, Am. J. Med. 105(3A):15S–21S [1998]; L. A. Jason et al., Estimating the prevalence of chronic fatigue syndrome among nurses, Am. J. Med. 105(3A):91S–93S [1998]). One study reported that there was no support for an etiological role in CFS of *Yersinia enterocolitica* infection. (C. M. Swanink et al., *Yersinia entercolitica* and the chronic fatigue syndrome, J. Infect. 36(3):269–72 [1998]). Accordingly, there has been no known cause to which diagnosis and/or treatment of CSF could be directed.

Consequently, the diagnosis and treatment of CFS have continued to be directed to symptoms, rather than to an underlying treatable cause. For example, the use of relaxin has been described for relaxing the involuntary muscles and thus relieve pain associated with CFS. (S. K. Yue, Method of treating myofascial pain syndrome with relaxin, U.S. Pat. No. 5,863,552).

Attention deficit/hyperactivity disorder (ADHD) is a heterogeneous behaviorial disorder of unknown etiology that always appears first in childhood, affecting 3–20% of elementary school-age children, and continues to affect up to 3% of adults. (Reviewed in L. L. Greenhill, Diagnosing attention deficit/hyperactivity disorder in children, J. Clin. Psychiatry 59 Suppl 7:31–41 [1998]). Those affected with ADHD symptoms typically exhibit inattentiveness and distractability (AD type), hyperactive and impulsive behavior (HI type), or a combination of these, to a degree that impairs normal functioning and is often socially disruptive. (M. L. Wolraich et al., Examination of DSM-IV criteria for attention deficit/hyperactivity disorder in a county-wide sample, J. Dev. Behav. Pediatr. 19(3):162–68 [1998]; J. J. Hudziak et al., Latent class and factor analysis of DSM-IV ADHD: a twin study of female adolescents, J. Am. Acad. Child Adolesc. Psychiatry 37(8):848–57 [1998]). Often prescribed are central nervous system stimulants, tricyclic antidepressants, antihypertensives, analgesics, or antimanic drugs, but there has been no known cause of ADHD to which diagnosis and/or treatment could be directed. (S. C. Schneider and G. Tan, Attention deficit/hyperactivity disorder. In pursuit of diagnostic accuracy, Postgrad. Med. 101 (4):23 1–2, 235–40 [1997]; W. J. Barbaresi, Primary-care approach to the diagnosis and management of attention deficit/hyperactivity disorder, Mayo Clin. Proc. 71(5):463–71 [1996]).

There has also been no known cause for autoimmune diseases, including multiple sclerosis and systemic lupus erythematosus. Multiple sclerosis (MS) is a neurologic disease that primarily strikes teens and young adults under 35 years. Affecting 350,000 Americans, MS is the most frequent cause of neurologic disability except for traumatic injuries; MS affects twice as many females compared to males. (S. L. Hauser, Multiple Sclerosis and other demyelinating diseases In: *Harrison's Principles of Internal Medicine,* 13th ed., K. J. Isselbacher et al. (eds.), McGraw-Hill, pp.2287–95 [1994]). The disease is characterized by chronic inflammation, scarring, and selective destruction of the myelin sheath around neural axons of the central nervous system, and is thought to be caused by autoimmune responses. A treatment for MS taught by Weiner et al. is related to oral administration of autoantigens to the patient to suppress the autoimmune response by eliciting suppressor T-cells specific for myelin basic protein (MBP). There are no specific diagnostic tests for MS; diagnosis is based on clinical recognition of destructive patterns of central nervous system injury that are produced by the disease. (S. L. Hauser [1994]) Nerve damage may be mediated by cytokines, especially TNF-α, which has been found to be selectively toxic to myelin and to oligodendrocytes in vitro. Elevated levels of TNF-α and IL-2 were measured in MS patients. (J. L. Trotter et al, Serum cytokine levels in chronic progressive multiple sclerosis: interleukin-2 levels parallel tumor necrosis factor-alpha levels, J. Neuroimmunol. 33(1):29–36 [1991]; H. L. Weiner et al., Treatment of multiple sclerosis by oral administration of autoantigens, U.S. Pat. No. 5,869,054). Another treatment for MS involves the administration of a vitamin D compound. (H. F. DeLuca et al., Multiple sclerosis treatment, U.S. Pat. No. 5,716,946). However, there has been no known cause of MS to which diagnosis and/or treatment could be directed.

Systemic lupus erythematosus (SLE) is an autoimmune rheumatic disease characterized by deposition in tissues of autoantibodies and immune complexes leading to tissue injury (B. L. Kotzin, Systemic lupus erythematosus, Cell 85:303–06 [1996]). In contrast to autoimmune diseases such as MS and type 1 diabetes mellitus, SLE potentially involves multiple organ systems directly, and its clinical manifestations are diverse and variable. (Reviewed by B. L. Kotzin and J. R. O'Dell, Systemic lupus erythematosus, In: *Samler's Immunologic Diseases,* 5th ed., M. M. Frank et al., eds., Little Brown & Co., Boston, pp. 667–97 [1995]). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide. (B. L. Kotzin [1996]).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (GN). (B. H. Hahn and B. Tsao, Antibodies to DNA, In: *Dubois' Lupus Erythematosus,* 4th ed., D. J. Wallace and B. Hahn, eds., Lea and Febiger, Philadelphia, pp. 195–201 [1993]; Ohnishi et al., Comparison of pathogenic and nonpathogenic murine antibodies to DNA: Antigen binding and structural characteristics, Int. Immunol. 6:817–30 [1994]). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause. (E.g., Hitoshi et al., Immunosuppressive agent, U.S. Pat. No. 4,843,092).

Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective. (Reviewed in V. A. Botoman et al., Management of Inflammatory Bowel Disease, Am. Fam. Physician 57(1):57–68 [1998]). Immunosuppression with cyclosporine is sometimes beneficial for patients resistant to or intolerant of corticosteroids. (J. Brynskov et al., A placebo-controlled, double-blind, randomized trial of cyclosprorine therapy in active chronic Crohn's disease, N. Engl. J. Med. 321(13):845–50 [1989]).

Nevertheless, surgical correction is eventually required in 90% of patients; 50% undergo colonic resection. (K. Leiper et al., Adjuvant post-operative therapy, Baillieres Clin. Gastroenterol. 12(1):179–99 [1998]; F. Makowiec et al., Long-term follow-up after resectional surgery in patients with Crohn's disease involving the colon, Z. Gastroenterol. 36(8):619–24 [1998]). The recurrence rate after surgery is high, with 50% requiring further surgery within 5 years. (K. Leiper et al. [1998]; M. Besnard et al., Postoperative outcome of Crohn 's disease in 30 children, Gut 43(5):634–38 [1998]).

One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Söderholm et al., Epithelial permeability to proteins in the non-inflamed ileum of Crohn's disease?, Gastroenterol. 117:65–72 [1999]; D. Hollander et al., Increased intestinal permeability in patients with Crohn's disease and their relatives. A possible etiologic factor, Ann. Intern. Med. 105:883–85 [1986]; D. Hollander, The intestinal permeability barrier. A hypothesis to its involvement in Crohn's disease, Scand. J. Gastroenterol. 27:721–26 [1992] ). Another hypothesis is that persistent intestinal infection by pathogens such as *Mycobacterium paratuberculosis, Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce. (R. B. Sartor, Pathogenesis and Immune Mechanisms of Chronic Inflammatory Bowel Diseases, Am. J. Gastroenterol. 92(12):5S–11S [1997]). The presence of IgA and IgG anti-*Saccharomyces cerevisiae* antibodies (ASCA) in the serum was found to be highly diagnostic of pediatric Crohn's disease. (F. M. Ruemmele et al., Diagnostic accuracy of serological assays in pediatric inflammatory bowel disease, Gastroenterol. 115(4):822–29 [1998]; E. J. Hoffenberg et al., Serologic testing for inflammatory bowel disease, J. Pediatr. 134(4):447–52 [1999]).

In Crohn's disease, a dysregulated immune response is skewed toward cell-mediated immunopathology. (S. I. Murch, Local and systemic effects of macrophage cytokines in intestinal inflammation, Nutrition 14:780–83 [1998]). But immunosuppressive drugs, such as cyclosporine, tacrolimus, and mesalamine have been used to treat corticosteroid-resistant cases of Crohn's disease with mixed success. (J. Brynskov et al. [1989]; K. Fellerman et al., Steroid-unresponsive acute attacks of inflammatory bowel disease: immunomodulation by tacrolimus [FK506], Am. J. Gastroenterol. 93(10):1860–66 [1998]).

Recent efforts to develop diagnostic and treatment tools against Crohn's disease have focused on the central role of cytokines. (S. Schreiber, Experimental immunomodulatory therapy of inflammatory bowel disease, Neth. J. Med. 53(6): S24–31 [1998]; R. A. van Hogezand and H. W. Verspaget, The future role of anti-tumour necrosis factor-alpha products in the treatment of Crohn's disease, Drugs 56(3):299–305 [1998]). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts. (Reviewed in G. Rogler and T. Andus, Cytokines in inflammatory bowel disease, World J. Surg. 22(4):382–89 [1998]; H. F. Galley and N. R. Webster, The immuno-inflammatory cascade, Br. J. Anaesth. 77:11–16 [1996]). Some cytokines are pro-inflammatory (e.g., tumor necrosis factor [TNF]-α, interleukin [IL]-1 (α and β), IL-6, IL-8, IL-12, or leukemia inhibitory factor [LIF]); others are anti-inflammatory (e.g., IL-1 receptor antagonist [IL-1ra], IL-4, IL-10, IL-11, and transforming growth factor [TGF]-β). However, there may be overlap and functional redundancy in their effects under certain inflammatory conditions.

In active cases of Crohn's disease, elevated concentrations of TNF-α and IL-6 are secreted into the blood circulation, and TNF-α, IL-1, IL-6, and IL-8 are produced in excess locally by mucosal cells. (Id.; K. Funakoshi et al., Spectrum of cytokine gene expression in intestinal mucosal lesions of Crohn's disease and ulcerative colitis, Digestion 59(1):73–78 [1998]). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease. (G. Rogler and T. Andus [1998]; T. Saiki et al., Detection of pro- and anti-inflammatory cytokines in stools of patients with inflammatory bowel disease, Scand. J. Gastroenterol. 33(6):616–22 [1998]; S. Dionne et al., Colonic explant production of IL-1 and its receptor antagonist is imbalanced in inflammatory bowel disease (IBD); Clin. Exp. Imunol. 112(3):435–42 [1998]; But see S. Kuboyama, Increased circulating levels of interleukin-1 receptor antagonist in patients with inflammatory bowel disease, Kurume Med. J. 45(1):33–37 [1998]). One study suggested that cytokine profiles in stool samples could be a useful diagnostic tool for Crohn's disease. (T. Saiki et al. [1998]).

Treatments that have been proposed for Crohn's disease include the use of various cytokine antagonists (e.g., IL-1ra), inhibitors (e.g., of IL-1β converting enzyme and antioxidants) and anti-cytokine antibodies. (G. Rogler and T. Andus [1998]; R. A. van Hogezand and H. W. Verspaget [1998]; J. M. Reimund et al., Antioxidants inhibit the in vitro production of inflammatory cytokines in Crohn's disease and ulcerative colitis, Eur. J. Clin. Invest. 28(2):145–50 [1998]; N. Lugering et al., Current concept of the role of monocytes/macrophages in inflammatory bowel disease-balance of pro-inflammatory and immunosuppressive mediators, Ital. J. Gastroenterol. Hepatol. 30(3):338–44 [1998]; M. E. McAlindon et al., Expression of interleukin 1 beta and interleukin 1 beta converting enzyme by intestinal macrophages in health and inflammatory bowel disease, Gut 42(2):214–19 [1998]). In particular, monoclonal antibodies against TNF-α have been tried with some success in the treatment of Crohn's disease. (S. R. Targan et al., A short-term study of chimeric monoclonal antibody cA2 to tumor necrosis factor alpha for Crohn's disease. Crohn's Disease cA2 Study Group, N. Engl. J. Med. 337(15): 1029–35 [1997]; W. A. Stack et al., Randomised controlled trial of CDP571 antibody to tumour necrosis factor-alpha in Crohn's disease, Lancet 349(9051):521–24 [1997]; H. M. van Dullemen et al., Treatment of Crohn's disease with anti-tumor necrosis factor chimeric monoclonal antibody (cA2), Gastroenterol. 109(1):129–35 [1995]).

Another approach to the treatment of Crohn's disease has focused on at least partially eradicating the bacterial community that may be triggering the inflammatory response and replacing it with a non-pathogenic community. For example, McCann et al. (McCann et al., Method for treatment of idiopathic inflammatory bowel disease, U.S. Pat. No. 5,599,795) disclosed a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (T. J. Barody, Treatment of gastro-intestinal disorders with a fecal composition or a composition of bacteroides and *E. coli*, U.S. Pat. No. 5,443,826). However, there has been no known cause of Crohn's disease to which diagnosis and/or treatment could be directed.

Pain is a common symptom associated with irritable bowel syndrome, fibromyalgia, chronic fatigue syndrome, depression, ADHD, autoimmune diseases, and Crohn's disease. While the experience of pain is intertwined with a person's emotions, memory, culture, and psychosocial situation (D. A. Drossman and W. G. Thompson, Irritable bowel syndrome: a graduated, multicomponent treatment approach, Ann. Intern. Med. 116:1009–16 [1992]), evidence shows that certain cytokine mediated-immune responses can influence the perception of pain. Cytokines can be released in response to a variety of irritants and can modulate the perception of pain. For example, exposure of human bronchial epithelial cells to irritants, including acidic pH, results in a receptor-mediated release of inflammatory cytokines IL-6, IL-8, and TNF-α. (B. Veronesi et al., Particulate Matter initiates inflammatory cytokine release by activation of capsaicin and acid receptors in a human bronchial epithelial cell line, Toxicol. Appl. Pharmacol. 154:106–15 [1999]). Irritant receptors on cell surfaces, e.g., receptors sensitive to noxious stimuli, such as capsaicin and pH, mediate the release of cytokines and also mediate the release of neuropeptides from sensory nerve fibers, which is known to result in a neurogenic inflammatory processes and hyperalgesia (excessive sensitivity to pain). (Id.; R. O. P. de Campos et al., Systemic treatment with *Mycobacterium bovis bacillus calmett-guerin*(BCG) potentiates kinin $B_1$ receptor agonist-induced nociception and oedema formation in the formalin test in mice, Neuropeptides 32(5):393403 [1998]).

The perception of pain, is also influenced by the mediation of kinin $B_1$ and $B_2$ receptors, which bind peptides called kinins, e.g., the nonapeptide bradykinin or the decapeptide kallidin (lysyl bradykinin). While the precise mechanism of action is unknown, kinins cause the release of other proinflammatory and hyperalgesic mediators such as neuropeptides. Cytokines IL-1 (α and β), IL-2, IL-6, and TNF-α are thought to activate kinin $B_1$ receptor, and thus can contribute to enhanced perception of pain. (R. O. P. de Campos et al. [1998]. The endotoxin of *Escherichia coli* significantly activated kinin $B_1$ receptor-mediated neurogenic and inflammatory pain responses in animals. (M. M. Campos et al., Expression of $B_1$ kinin receptors mediating paw oedema formalin-induced nociception. Modulation by glucocorticoids, Can. J. Physiol. Pharmacol. 73:812–19 [1995]).

It has also been shown that IL-1β, IL6, and TNF-α, administered to the mammalian brain, can modulate pain perception via prostaglandin-dependent processes. (T. Hori et al., Pain modulatory actions of cytokines and prostaglandin $E_2$ in the Brain, Ann. N. Y. Acad. Sci. 840:269–81 [1998]). Granulocytes, which accumulate in nearly all forms of inflammation, are non-specific amplifiers and effectors of specific immune responses, and they can also modulate the perception of pain. Neutrophils, a type of granulocyte cell, are known to accumulate in response to IL-1β, and neutrophil accumulation plays a crucial positive role in the development of nerve growth factor (NGF)-induced hyperalgesia. (G. Bennett et al., Nerve growth factor induced hyperalgesia in the rat hind paw is dependent on circulating neutrophils, Pain 77(3):315–22 [1998]; see also E. Feher et al., Direct morphological evidence of neuroimmunomodulation in colonic mucosa of patients with Crohn's disease, Neuroimmunomodulation 4(5–6):250–57 [1997]).

Hyperalgesia (visceral, musculoskeletal, and/or cutaneous) is a common clinical observation in IBS and fibromyalgia. As many as 60% of subjects with IBS have reduced sensory thresholds for rectal distension. (H. Mertz et al., Altered rectal perception is a biological marker of patients with the irritable bowel syndrome, Gastroenterol. 109:40–52 [1995]). While the etiology for this hyperalgesia has remained elusive, it has been hypothesized that there is a sensitization of afferent pathways in IBS. (E. A. Mayer et al., Basic and clinical aspects of visceral hyperalgesia, Gastroenterol 1994;107:271–93 [1994]; L. Bueno et al., Mediators and pharmacology of visceral sensitivity: from basic to clinical investigations, Gastroenterol. 112:171–443 [1997]). Fibromyalgia is, by definition; a hyperalgesic state since the American College of Rheumatology defines fibromyalgia as a history of global pain in the setting of 11 out of 18 predefined tender points. (F. Wolfe et al., The American College of Rheumatology 1990 criteria for the classification of fibromyalgia, Arthritis Rheum. 33:160–72 [1990]). Evidence implies that the hyperalgesia of fibromyalgia is not simply trigger point-related but rather a global hyperalgesia. (L. Vecchiet et al., Comparative sensory evaluation of parietal tissues in painful and nonpainful areas in fibromyalgia and myofascial pain syndrome, In: Gebhart G F, Hammond D L, Jensen T S, editors, Progress in Pain Research and Management, Vol. 2, Seattle: IASP Press, pp.177–85 [1994]; J. Sorensen et al., Hyperexcitability in fibromyalgia, J. Rheumatol. 25:152–55 [1998]).

While hyperalgesia has not been clearly shown to be associated with Crohn's disease (C. N. Bernstein et al., Rectal afferent function in patients with inflammatory and functional intestinal disorders, Pain 66:151–61 [1996]), cytokine and neuropeptide levels are altered in IBS, fibromyalgia, and Crohn's disease. Indirect evidence for hypersensitivity in Crohn's disease is suggested by elevated TNF-α and substance P receptor levels (C. R. Mantyh et al., Receptor binding sites for substance P, but not substance K or neuromedin K, are expressed in high concentrations by arterioles, venules, and lymph nodules in surgical specimens obtained from patients with ulcerative colitis and Crohn's disease, Proc. Natl. Acad. Sci. 85:3235–39 [1988]; S. Mazumdar and K. M. Das, Immunocytochemical localization of vasoactive intestinal peptide and substance P in the colon from normal subjects and patients with inflammatory bowel disease, Am. J. Gastrol. 87:176–81 [1992]; C. R. Mantyh et al., Differential expression of substance P receptors in patients with Crohn's disease and ulcerative colitis, Gastroenterol. 1995;109:850–60 [1995]), which have been shown to be associated with hypersensitivity. It has been shown that levels of substance P, a neuropeptide, are elevated in the cerebrospinal fluid of subjects with fibromyalgia (H. Vaeroy et al., Elevated CSF levels of substance P and high incidence of Raynaud's phenomenon in patients with fibromyalgia: new features for diagnosis, Pain 32:21–26 [1988]; I. J. Russell et al., Elevated cerebrospinal fluid levels of substance P in patients with the fibromyalgia syndrome, Arthritis Rheum. 37:1593–1601 [1994]), and an increase in substance P-sensitive nerve endings has been observed in subjects with IBS. (X. Pang et al., Mast cell substance P-positive nerve involvement in a patient with both irritable bowel syndrome and interstitial cystitis, Urology 47:436–38 [1996]).

Mental functioning and feelings of fatigue or depression can also be influenced by immune responses. Peripherally released pro-inflammatory cytokines, such as IL-1, IL-6 and TNF-α, act on brain cellular targets and have been shown to depress spontaneous and learned behavior in animals; the vagus nerve has been shown to mediate the transmissions of the immune message to the brain, resulting in production of pro-inflammatory cytokines centrally in the brain. (R. Dantzer et al., Cytokines and sickness behavior, Ann. N. Y. Acad. Sci. 840:586–90 [1998]). In addition, there is bidirectional interplay between neurotransmitters and the immune system; lymphocytes and macrophages bear surface receptors for the stress hormone corticotrophin releasing hormone (CRH), and they respond to CRH by enhanced lymphocyte proliferation and feedback upregulation of hypothalamic CRH production. (S. H. Murch [1998]).

Pituitary production of proopiomelanocortins, such as endorphins and enkephalins, is upregulated by IL-1 and IL-2, possibly mediated by CRH, and lymphocytes and macrophages recognize these endogenous opiates via surface receptors. (S. H. Murch [1998]). Lymphocytes ($T_H2$) and macrophages also produce and process enkephalin to an active form. Macrophage-derived cytokines, such as TNF-α, IL-1, and IL-6, are known to modulate neurotransmitter release and to affect overall neural activity; cytokines can induce classic illness behavior such as somnolence, apathy, depression, irritability, confusion, poor memory, impaired mental concentration, fever and anorexia.

While immunological responses can lead to symptoms of irritable bowel syndrome, fibromyalgia, chronic fatigue syndrome, depression, ADHD, autoimmune diseases, and Crohn's disease, there has been a definite need to determine a causal factor, for each of these diagnostic categories, to which diagnostic testing and treatment can be directed.

No association has ever been made between any of the afore-going diagnostic categories and small intestinal bacterial overgrowth (SIBO). SIBO, also known as small bowel bacterial overgrowth (SBBO), is an abnormal condition in which aerobic and anaerobic enteric bacteria from the colon proliferate in the small intestine, which is normally relatively free of bacterial contamination. SIBO is defined as greater than $10^6$ CFU/mL small intestinal effluent (R. M. Donaldson, Jr., Normal bacterial populations of the intestine and their relation to intestinal function, N. Engl. J. Med. 270:93845 [1964]). Typically, the symptoms include abdominal pain, bloating, gas and alteration in bowel habits, such as constipation and diarrhea.

SIBO has, until recently, mostly been suspected in subjects with significant malabsorptive sequelae. Most of the described cases of SIBO involve anatomic alterations such as physical obstruction (E. A. Deitch et al., Obstructed intestine as a reservoir for systemic infection, Am. J. Surg.159:394 [1990]), surgical changes (e.g., L. K. Enander et al., The aerobic and anaerobic microflora of the gastric remnant more than 15 years after Billroth II resection, Scand. J. Gastroenterol. 17:715–20 [1982]), direct communication of the small intestine with colonic contents such as fistulae (O. Bergesen et al., Is vitamin B12 malabsorption in bile fistula rats due to bacterial overgrowth? A study of bacterial metabolic activity in the small bowel, Scand. J. Gastroenterol. 23:471–6 [1988]) and ileocecal valve dysfunction (surgical or otherwise) (W. O. Griffin, Jr, et al., Prevention of small bowel contamination by ileocecal valve, S. Med. J.64: 1056–8 [1971]; P. Rutgeerts et al., Ileal dysfunction and bacterial overgrowth in patients with Crohn's disease, Eur. J. Clin. Invest. 11: 199–206 [1981]). Less commonly, SIBO has been associated with chronic pancreatitis (E. Trespi and A. Ferrieri, Intestinal bacterial overgrowth during chronic pancreatitis, Curr. Med. Res. Opin. 15:47–52 [1999]), hypochlorhydria (e.g., S. P. Pereira et al., Drug-induced hypochlorhydria causes high duodenal bacterial counts in the elderly, Aliment. Pharmacol. Ther.12:99–104 [1998]), and immunodeficiency (C. Pignata et al., Jejunal bacterial overgrowth and intestinal permeability in children with immunodeficiency syndromes, Gut 31:879–82 [1990]; G. M. Smith et al., Small intestinal bacterial overgrowth in patients with chronic lymphocytic leukemia, J. Clin. Pathol. 43:57–9 [1990]).

SIBO has been associated with infections of the abdominal cavity in cases of alcoholic cirrhosis. (F. Casafont Morencos et al., Small bowel bacterial overgrowth in patients with alcoholic cirrhosis, Dig. Dis. Sci. 40(6): 1252–1256 [1995]; J. Chesta et al., Abnormalities in proximal small bowel motility in patients with cirrhosis, Hepatology 17(5):828–32 [1993]; C. S. Chang et al., Small intestine dysmotility and bacterial overgrowth in cirrhotic patients with spontaneous bacterial peritonitis, Hepatology 28(5):1187–90 [1998]). SIBO has also been associated with symptoms of chronic diarrhea, anorexia or nausea in elderly patients, and the prevalence of overgrowth in subjects over 75 years old is reported to be as high as 79% even in the absence of clinically evident clues of overgrowth or achlorhydria. (S. M. Riordan et al., Small intestinal bacterial overgrowth in the symptomatic elderly, Am. J. Gastroenterol. 92(1):47–51 [1997]). SIBO is also associated with chronic digestive symptoms in children, especially infants under two years of age (D. De Boissieu et al., Small-bowel bacterial overgrowth in children with chronic digestive diarrhea, abdominal pain, or both, J. Pediatr. 128(2):203–07 [1996]), and with chronic diarrhea after liver transplantation in children. (D. R. Mack et al., Small bowel bacterial overgrowth as a cause of chronic diarrhea after liver transplantation in children, Liver Transpl. Surg. 4(2):166–69 [1998]).

Although diabetic enteropathy (F. Goldstein et al., Diabetic diarrhea and steatorrhea. Microbiologic and clinical observations, Ann. Intern. Med. 1970;72:215–8 [1970]), idiopathic intestinal pseudo-obstruction (A. J. Pearson et al., Intestinal pseudo-obstruction with bacterial overgrowth in the small intestine, Am. J. Dig. Dis. 14:200–05 [1969]) and scleroderma (I. J. Kahn et al., Malabsorption in intestinal scleroderma: Correction with antibiotics, N. Engl. J. Med. 274: 133944 [1966]) are all known to produce motility disturbances leading to SIBO. Two previous reports have examined small bowel motility among anatomically and medically naive SIBO subjects. (G. Vantrappen et al., The interdigestive motor complex of normal subjects and patients with bacterial overgrowth of the small intestine, J. Clin. Invest. 59: 1158–66 [1977]; P. O. Stotzer et al., Interdigestive and postprandial motility in small-intestinal bacterial overgrowth, Scand. J. Gastroenterol. 31:875–80 [1996]). These authors suggest that the majority of subjects with SIBO in the absence of other predisposing conditions, lack the phase III of interdigestive motility during short term recordings.

Phase III of interdigestive motility is a period of phasic contractions propagating through the length of the small intestine, approximately once every 87.2±5.4 minutes in the fasting state. (E. E. Soffer et al., Prolonged ambulatory duodeno-jejunal manometry in humans: Normal values and gender effect, Am. J. Gastrol. 93:1318–23 [1998]). This fasting event is responsible for sweeping residue including small bowel contaminants, such as accumulated bacteria, into the colon in preparation for the next meal. (V. B. Nieuwenhujuijs et al., The role of interdigestive small bowel motility in the regulation of gut microflora, bacterial overgrowth, and bacterial translocation in rats, Ann. Surg. 228: 188–93 [1998]; E. Husebye, Gastrointestinal motility disorders and bacterial overgrowth, J. Intern. Med. 237:419–27 [1995]). The endogenous peptide, motilin, is involved in the mediation of this event. (G. Vantrappen et al., Motilin and the interdigestive migrating motor complex in man, Dig. Dis. Sci. 24:497–500 [1979]). Other prokinetic agents, such as erythromycin, are believed to act on the motilin receptor and have been shown to rapidly induce an interdigestive motility event in dogs and humans. (M. F. Otterson and S. K. Sarna, Gastrointestinal motor effect of erythromycin, Am. J. Physiol. 259:G355–63; T. Tomomasa et al., Erythromycin induces migrating motor complex in human gastrointestinal tract, Dig. Dis. Sci. 31:157–61 [1986]).

There remains a need for an underlying causal factor, to which diagnostic testing and treatment can be directed, for irritable bowel syndrome; fibromyalgia; chronic fatigue syndrome; depression; ADHD; MS, SLE and other autoimmune diseases; and Crohn's disease. This and other benefits of the present invention are described herein.

SUMMARY OF THE INVENTION

The present invention relates to the diagnosis or treatment of irritable bowel syndrome (IBS); fibromyalgia (FM); chronic fatigue syndrome (CFS); depression; attention deficit/hyperactivity disorder (ADHD); multiple sclerosis (MS), systemic lupus erythematosus (SLE) and other autoimmune diseases; and Crohn's disease (CD). Specifically, the present methods are based on the detection and treatment of a unified cause for all of them, i.e., small intestinal bacterial overgrowth (SIBO).

The method of diagnosing irritable bowel syndrome, fibromyalgia, chronic fatigue syndrome, depression, ADHD, autoimmune diseases, or Crohn's disease involves detecting the presence of small intestinal bacterial overgrowth in a human subject having at least one symptom associated with a suspected diagnosis of any of those diagnostic categories.

The present invention also relates to a method of treatment for irritable bowel syndrome, fibromyalgia, chronic fatigue syndrome, depression, ADHD, autoimmune diseases, or Crohn's disease involving a therapeutic regime to at least partially eradicate small intestinal bacterial overgrowth. This therapy regime can include treatment with anti-microbial agents or other therapeutic approaches to at least partially eradicating bacterial overgrowth, e.g., lavage, probiotic techniques, or by normalizing or increasing intestinal phase III interdigestive motility with, for example, administration of a modified diet or a chemical prokinetic agent. The method improves symptoms, including hyperalgesia related to SIBO and disorders caused by SIBO, such as irritable bowel syndrome, fibromyalgia, and Crohn's disease.

The present invention also relates to kits for the diagnosis and treatment of irritable bowel syndrome, fibromyalgia, chronic fatigue syndrome, depression, ADHD, autoimmune diseases, or Crohn's disease.

These and other advantages and features of the present invention will be described more fully in a detailed description of the preferred embodiments which follows.

DETAILED DESCRIPTION OF THE PREFERRED EMBODIMENTS

Figure 1:
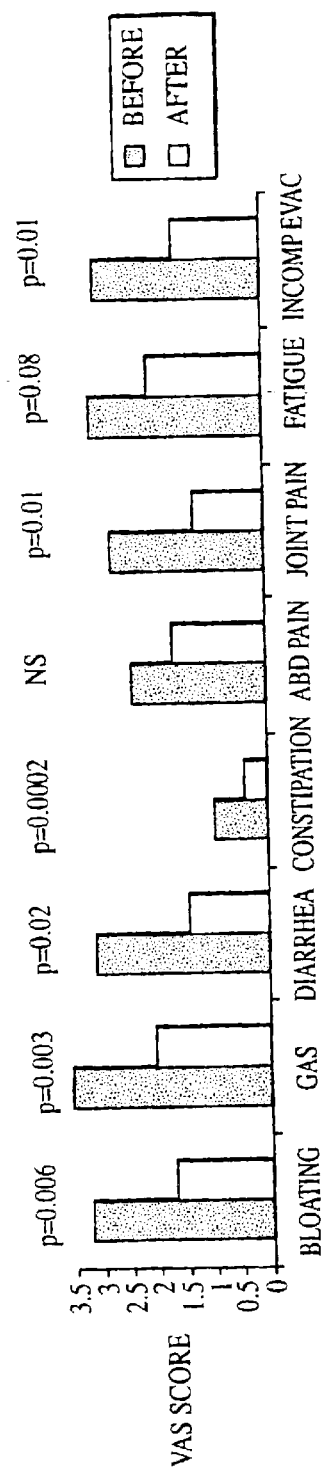
FIG. 1 shows visual analog scores reported by subjects with IBS and SIBO before and after antibiotic treatment.

The present invention relates to method of diagnosing irritable bowel syndrome, fibromyalgia, chronic fatigue syndrome, depression, ADHD, an autoimmune disease, such as multiple sclerosis or systemic lupus erythematosus, or Crohn's disease. The method involves detecting the presence of small intestinal bacterial overgrowth in a human subject who has at least one symptom associated with a suspected diagnosis of any one of these diagnostic categories.

In accordance with the method, the detection of SIBO in the human subject corroborates the suspected diagnosis held by a qualified medical practitioner who, prior to the detection of SIBO in the human subject, suspects from more limited clinical evidence that the human subject has irritable bowel syndrome, fibromyalgia, chronic fatigue syndrome, depression, ADHD, an autoimmune disease, or Crohn's disease. By applying the present diagnostic method the suspected diagnosis is corroborated, i.e., confirmed, sustained, substantiated, supported, evidenced, strengthened, affirmed or made more firm.

The skilled medical practitioner is aware of suitable up-to-date diagnostic criteria by which a suspected diagnosis is reached. These diagnostic criteria are based on a presentation of symptom(s) by a human subject. For example, these criteria include, but are not limited to, the Rome criteria for IBS (W. G. Thompson, Irritable bowel syndrome: pathogenesis and management, Lancet 341:1569–72 [1993]) and the criteria for CFS established by the Centers for Disease Control and Prevention (CDC). (K. Fukuda et al., The chronic fatigue syndrome: a comprehensive approach to its definition and study, Ann. Intern. Med. 121:953 –59 [1994]). The diagnostic criteria for fibromyalgia of the American College of Rheumatology will also be familiar (F. Wolfe et al., The American College of Rheumatology 1990 Criteria for the Classification of Fibromyalgia: Report of the Multicenter Criteria Committee, Arthritis Rheum. 33:160–72 [1990]), as will be the criteria for depression or ADHD provided for example, by the Diagnostic and Statistical Manual (DSM)-IV or its current version. (E.g., G. Tripp et al., DSM-IV and ICD-10: a comparison of the correlates of ADHD and hyperkinetic disorder, J. Am. Acad. Child Adolesc. Psychiatry 38(2):156–64 [1999]). Symptoms of systemic lupus erythematosus include the 11 revised criteria of the American College of Rheumatology, such as a typical malar or discoid rash, photosensitivity, oral ulcers, arthritis, serositis, or disorders of blood, kidney or nervous system. (E. M Tan et al., The 1982 revised criteria for the classification of systemic lupus erythematosus [SLE], Arthritis Rheum. 25:1271–77 [1982]). Appropriate diagnostic criteria for multiple sclerosis are also familiar (e.g., L. A. Rolak, The diagnosis of multiple sclerosis, Neuronal Clin. 14(1):27–43 [1996]), as are symptoms of Crohn's disease useful in reaching a suspected diagnosis. (e.g., J. M. Bozdech and R. G. Farmer, Diagnosis of Crohn's disease, Hepatogastroenterol. 37(1):8–17 [1990]; M. Tanaka and R. H. Riddell, The pathological diagnosis and differential diagnosis of Crohn's disease, Hepatogastroenterol. 37(1):18–31 [1990]; A. B. Price and B. C. Morson, inflammatory bowel disease: the surgical pathology of Crohn's disease and ulcerative colitis, Hum. Pathol. 6(1):7–29 [1975]). The practitioner is, of course not limited to these illustrative examples for diagnostic criteria, but should use criteria that are current.

Detecting the presence of small intestinal bacterial overgrowth (i.e., SIBO) is accomplished by any suitable method. For example, one preferred method of detecting SIBO is breath hydrogen testing. (E.g., P. Kerlin and L. Wong, Breath hydrogen testing in bacterial overgrowth of the small intestine, Gastroenterol. 95(4):982–88 [1988]; A. Strocchi et al., Detection of malabsorption of low doses of carbohydrate: accuracy of various breath $H_2$ criteria, Gastroenterol. 105(5):1404–1410 [1993]; D. de Boissieu et al., [1996]; P. J. Lewindon et a., Bowel dysfunction in cysticfibrosis: importance of breath testing, J. Paedatr. Child Health 34(1):79–82 [1998]). Breath hydrogen or breath methane tests are based on the fact that many obligately or facultatively fermentative bacteria found in the gastrointestinal tract produce detectable quantities of hydrogen or methane gas as fermentation products from a substrate consumed by the host, under certain circumstances. Substrates include sugars such as lactulose, xylose, lactose, or glucose. The hydrogen or methane produced in the small intestine then enters the blood stream of the host and are gradually exhaled.

Typically, after an overnight fast, the patient swallows a controlled quantity of a sugar, such as lactulose, xylose, lactose, or glucose, and breath samples are taken at frequent time intervals, typically every 10 to 15 minutes for a two- to four-hour period. Samples are analyzed by gas chromatography or by other suitable techniques, singly or in combination. Plots of breath hydrogen in patients with SIBO typically show a double peak, i.e., a smaller early hydrogen peak followed by a larger hydrogen peak, but a single hydrogen peak is also a useful indicator of SIBO, if peak breath hydrogen exceeds the normal range of hydrogen for a particular testing protocol. (See, G. Mastropaolo and W. D. Rees, Evaluation of the hydrogen breath test in man: definition and elimination of the early hydrogen peak, Gut 28(6):721–25 [1987]).

A variable fraction of the population fails to exhale appreciable hydrogen gas during intestinal fermentation of lactulose; the intestinal microflora of these individuals instead produce more methane. (G. Coraza et al., Prevalence and consistency of low breath $H_2$ excretion following lactulose ingestion. Possible implications for the clinical use of the $H_2$ breath test, Dig. Dis. Sci. 38(11):2010–16 [1993]; S. M. Riordan et al., The lactulose breath hydrogen test and small intestinal bacterial overgrowth, Am. J. Gastroentrol. 91(9); 1795–1803 [1996]). Consequently, in the event of an initial negative result for breath hydrogen, or as a precaution, methane and/or carbon dioxide contents in each breath sample are optionally measured, as well as hydrogen, or a substrate other than lactulose is optionally used. Also, acting as a check, the presence of SIBO is demonstrated by a relative decrease in peak hydrogen exhalation values for an individual subject after antimicrobial treatment, in accordance with the present invention, compared to pretreatment values.

Another preferred method of detecting bacterial overgrowth is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human host, such as lactulose, xylose, mannitol, or urea. (E.g., G. R. Swart and J. W. van den Berg, $^{13}C$ breath test in gastrointestinal practice, Scand. J. Gastroenterol. [Suppl.] 225:13–18 [1998]; S. F. Dellert et al., The 13C-xylose breath test for the diagnosis of small bowel bacterial overgrowth in children, J. Pediatr. Gastroenterol. Nutr. 25(2):153–58 [1997]; C. E. King and P. P. Toskes, Breath tests in the diagnosis of small intestinal bacterial overgrowth, Crit. Rev. Lab. Sci. 21(3):269–81 [1984]). A poorly digestible substrate is one for which there is a relative or absolute lack of capacity in a human for absorption thereof or for enzymatic degradation or catabolism thereof.

Suitable isotopic labels include $^{13}C$ or $^{14}C$. For measuring methane or carbon dioxide, suitable isotopic labels can also include $^2H$ and $^3H$ or $^{17}O$ and $^{18}O$, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}C$, $^3H$, or $^{15}O$, breath samples can be analyzed by gas chromatography with suitable radiation detection means. (E.g., C. S. Chang et al., Increased accuracy of the carbon-14 D-xylose breath test in detecting small-intestinal bacterial overgrowth by correction with the gastric emptying rate, Eur. J. Nucl. Med. 22(10):1118–22 [1995]; C. E. King and P. P. Toskes, Comparison of the 1-gram [$^{14}C$]xylose, 10-gram lactulose-$H_2$, and 80-gram glucose-$H_2$ breath tests in patients with small intestine bacterial overgrowth, Gastroenterol. 91(6):1447–51 [1986]; A. Schneider et al., Value of the $^{14}C$-D-xylose breath test in patients with intestinal bacterial overgrowth, Digestion 32(2):86–91 [1985]).

Another preferred method of detecting small intestinal bacterial overgrowth is direct intestinal sampling from the human subject. Direct sampling is done by intubation followed by scrape, biopsy, or aspiration of the contents of the intestinal lumen, including the lumen of the duodenum, jejunum, or ileum. The sampling is of any of the contents of the intestinal lumen including material of a cellular, fluid, fecal, or gaseous nature, or sampling is of the lumenal wall itself. Analysis of the sample to detect bacterial overgrowth is by conventional microbiological techniques including microscopy, culturing, and/or cell numeration techniques.

Another preferred method of detecting small intestinal bacterial overgrowth is by endoscopic visual inspection of the wall of the duodenum, jejunum, and/or ileum.

The preceding are merely illustrative and non-exhaustive examples of methods for detecting small intestinal bacterial overgrowth.

The present invention also relates to a method of treating irritable bowel syndrome, fibromyalgia, chronic fatigue syndrome, depression, ADHD, an autoimmune disease, or Crohn's disease. The treatment method involves detecting the presence of small intestinal bacterial overgrowth in a human subject, in accordance with the diagnostic method described above, and at least partially eradicating the bacterial overgrowth. After the SIBO condition is at least partially eradicated, typically within a couple of weeks, there is an improvement in the symptom(s) of irritable bowel syndrome, fibromyalgia, chronic fatigue syndrome, depression, ADHD, an autoimmune disease, or Crohn's disease. It is a benefit of the present treatment method that after treatment, subjects routinely report feeling better than they have felt in years.

At least partially eradicating the bacterial overgrowth is accomplished by any suitable method. Most preferably, at least partially eradicating the bacterial overgrowth is accomplished by administering an antimicrobial agent, including but not limited to a natural, synthetic, or semi-synthetic antibiotic agent. For example, a course of antibiotics such as, but not limited to, neomycin, metronidazole, teicoplanin, doxycycline, tetracycline, ciprofloxacin, augmentin, cephalexin (e.g., Keflex), penicillin, ampicillin, kanamycin, rifamycin, rifaximin, or vancomycin, which may be administered orally, intravenously, or rectally. (R. K. Cleary [1998]; C. P. Kelly and J. T. LaMont, Clostridium difficile infection, Annu. Rev. Med. 49:375–90 [1998]; C. M. Reinke and C. R. Messick, Update on Clostridium difficile-induced colitis, Part 2, Am. J. Hosp. Pharm. 51(15):1892–1901 [1994]).

Alternatively, an antimicrobial chemotherapeutic agent, such as a 4- or 5-aminosalicylate compound is used to at least partially eradicate the SIBO condition. These can be formulated for ingestive, colonic, or topical non-systemic delivery systems or for any systemic delivery systems. Commercially available preparations include 4-(p)-aminosalicylic acid (i.e., 4-ASA or para-aminosalicylic acid) or 4-(p)-aminosalicylate sodium salt (e.g., Nemasol-Sodium® or Tubasal®). 5-Aminosalicylates have antimicrobial, as well as anti-inflammatory properties (H. Lin and M. Pimentel, Abstract G3452 at Digestive Disease Week, 100$^{th}$ Annual Meeting of the AGA, Orlando, Fla. [1999]), in useful preparations including 5-aminosalicylic acid (i.e., 5-ASA, mesalamine, or mesalazine) and conjugated derivatives thereof, available in various pharmaceutical preparations such as Asacol®, Rowasa®, Claversal®, Pentasa®, Salofalk®, Dipentum® (olsalazine), Azulfidine® (SAZ; sulphasalazine), ipsalazine, salicylazobenzoic acid, balsalazide, or conjugated bile acids, such as ursodeoxycholic acid-5-aminosalicylic acid, and others.

Another preferred method of at least partially eradicating small intestinal bacterial overgrowth, particularly useful when a subject does not respond well to oral or intravenous antibiotics or other antimicrobial agents alone, is administering an intestinal lavage or enema, for example, small bowel irrigation with a balanced hypertonic electrolyte solution, such as Go-lytely or fleet phosphosoda preparations. The lavage or enema solution is optionally combined with one or more antibiotic(s) or other antimicrobial agent(s). (E.g., J. A. Vanderhoof et al., Treatment strategies for small bowel bacterial overgrowth in short bowel syndrome, J. Pediatr. Gastroenterol. Nutr. 27(2):155–60 [1998])

Another preferred method of at least partially eradicating small intestinal bacterial overgrowth employs a probiotic agent, for example, an inoculum of a lactic acid bacterium or bifidobacterium. (A. S. Naidu et al., Probiotic spectra of lactic acid bacteria, Crit. Rev. Food Sci. Nutr. 39(1):13–126 [1999]; J. A. Vanderhoof et al. [1998]; G. W. Tannock, Probiotic propertyies of lactic acid bacteria: plenty of scope for R & D, Trends Biotechnol. 15(7):270–74 [1997]; S. Salminen et al., Clinical uses of probiotics for stabilizing the gut mucosal barrier: successful strains and future challenges, Antonie Van Leeuwenhoek 70(2–4):347–58 [1997]). The inoculum is delivered in a pharmaceutically acceptable ingestible formulation, such as in a capsule, or for some subjects, consuming a food supplemented with the inoculum is effective, for example a milk, yoghurt, cheese, meat or other fermentable food preparation. Useful probiotic agents include *Bifidobacterium* sp. or *Lactobacillus* species or strains, e.g., *L. acidophilus, L. rhamnosus, L. plantarum, L. reuteri, L. paracasei* subsp. *paracasei*, or *L. casei* Shirota, (P. Kontula et al., The effect of lactose derivatives on intestinal lactic acid bacteria, J. Dairy Sci. 82(2):249–56 [1999]; M. Alander et al., The effect of probiotic strains on the microbiota of the Simulator of the Human Intestinal Microbial Ecosystem (SHIME), Int. J. Food Microbiol. 46(1):71–79 [1999]; S. Spanhaak et al., The effect of consumption of milk fermented by Lactobacillus casei strain Shirota on the intestinal microflora and immune parameters in humans, Eur. J. Clin. Nutr. 52(12):899–907 [1998]; W. P. Charteris et al., Antibiotic susceptibility of potentially probiotic *Lactobacillus* species, J. Food Prot. 61(12):163643 [1998]; B. W. Wolf et al., Safety and tolerance of *Lactobacillus reuteri* supplementation to a population infected with the human immunodeficiency virus, Food Chem. Toxicol. 36(12):1085–94 [1998]; G. Gardiner et al., Development of a probiotic cheddar cheese containing human-derived *Lactobacillus paracasei* strains, Appl. Environ. Microbiol. 64(6):2192–99 [1998]; T. Sameshima et al., Effect of intestinal *Lactobacillus* starter cultures on the behaviour of *Staphylococcus aureus* in fermented sausage, Int. J. Food Microbiol. 41(1):1–7 [1998]).

Optionally, after at least partial eradication of small intestinal bacterial overgrowth, use of antimicrobial agents or probiotic agents can be continued to prevent further development or relapse of SIBO.

Another preferred method of at least partially eradicating small intestinal bacterial overgrowth is by normalizing or increasing phase III interdigestive intestinal motility with any of several modalities to at least partially eradicate the bacterial overgrowth, for example, by suitably modifying the subject's diet to increase small intestinal motility to a normal level (e.g., by increasing dietary fiber), or by administration of a chemical prokinetic agent to the subject, including bile acid replacement therapy when this is indicated by low or otherwise deficient bile acid production in the subject.

For purposes of the present invention, a prokinetic agent is any chemical that causes an increase in phase III interdigestive motility of a human subject's intestinal tract. Increasing intestinal motility, for example, by administration of a chemical prokinetic agent, prevents relapse of the SIBO condition, which otherwise typically recurs within about two months, due to continuing intestinal dysmotility. The prokinetic agent causes an in increase in phase III interdigestive motility of the human subject's intestinal tract, thus preventing a recurrence of the bacterial overgrowth. Continued administration of a prokinetic agent to enhance a subject's phase III interdigestive motility can extend for an indefinite period as needed to prevent relapse of the SIBO condition.

Preferably, the prokinetic agent is a known prokinetic peptide, such as motilin, or functional analog thereof, such as a macrolide compound, for example, erythromycin (50 mg/day to 2000 mg/day in divided doses orally or I.V. in divided doses), or azithromycin (250–1000 mg/day orally).

However, a bile acid, or a bile salt derived therefrom, is another preferred prokinetic agent for inducing or increasing phase III interdigestive motility. (E. P. DiMagno, Regulation of interdigestive gastrointestinal motility and secretion, Digestion 58 Suppl. 1:53–55 [1997]; V. B. Nieuwenhuijs et al., Disrupted bile flow affects interdigestive small bowel motility in rats, Surgery 122(3):600–08 [1997]; P. M. Hellstrom et al., Role of bile in regulation of gut motility, J. Intern. Med. 237(4):395402 [1995]; V. Plourde et al., Interdigestive intestinal motility in dogs with chronic exclusion of bile from the digestive tract, Can. J. Physiol. Pharmacol. 65(12):2493–96 [1987]). Useful bile acids include ursodeoxycholic acid and chenodeoxycholic acid; useful bile salts include sodium or potassium salts of ursodeoxycholate or chenodeoxycholate, or derivatives thereof.

A compound with cholinergic activity, such as cisapride (i.e., Propulsid®; 1 to 20 mg, one to four times per day orally or I.V.), is also preferred as a prokinetic agent for inducing or increasing phase III interdigestive motility. Cisapride is particularly effective in alleviating or improving hyperalgesia related to SIBO or associated with disorders caused by SIBO, such as IBS, fibromyalgia, or Crohn's disease.

A dopamine antagonist, such as metoclopramide (1–10 mg four to six times per day orally or I.V.), domperidone (10 mg, one to four times per day orally), or bethanechol (5 mg/day to 50 mg every 3–4 hours orally; 5–10 mg four times daily subcutaneously), is another preferred prokinetic agent for inducing or increasing phase III interdigestive motility. Dopamine antagonists, such as domperidone, are particularly effective in alleviating or improving hyperalgesia related to SIBO or associated with disorders caused by SIBO, such as IBS, fibromyalgia, or Crohn's disease.

Also preferred is a nitric oxide altering agent, such as nitroglycerin, nomega-nitro-L-arginine methylester (L-NAME), N-monomethyl-L-arginine (L-NMMA), or a 5-hydroxytryptamine (HT or serotonin) receptor antagonist, such as ondansetron (2–4 mg up to every 4–8 hours I.V.; pediatric 0.1 mg/kg/day) or alosetron. The 5-HT receptor antagonists, such as ondansetron and alosetron, are particularly effective in improving hyperalgesia related to SIBO, or associated with disorders caused by SIBO, such as IBS, fibromyalgia, or Crohn's disease.

An antihistamine, such as promethazine (oral or I.V. 12.5 mg/day to 25 mg every four hours orally or I.V.), meclizine (oral 50 mg/day to 100 mg four times per day), or other antihistamines, except ranitidine (Zantac), famotidine, and nizatidine, are also preferred as prokinetic agents for inducing or increasing phase III interdigestive motility.

Also preferred are neuroleptic agents, including prochlorperazine (2.5 mg/day to 10 mg every three hours orally; 25 mg twice daily rectally; 5 mg/day to 10 mg every three hours, not to exceed 240 mg/day intramuscularly; 2.5 mg/day to 10 mg every four hours I.V.), chlorpromazine (0.25 mg/lb. up to every four hours [5–400 mg/day] orally; 0.5 mg/lb. up to every 6 hours rectally; intramuscular 0.25/lb. every six hours, not to exceed 75/mg/day), or haloperidol (oral 5–10 mg/day orally; 0.5–10 mg/day I.V.). Also useful as a prokinetic agent, for purposes of the present invention, is a kappa agonist, such as fedotozine (1–30 mg/day), but not excluding other opiate agonists. The opiate (opioid) agonists, such as fedotozine, are particularly effective in alleviating or improving hyperalgesia related to SIBO or associated with disorders caused by SIBO, such as IBS, fibromyalgia, or Crohn's disease.

The preceding are merely illustrative of the suitable means by which small intestinal bacterial overgrowth is at least partially eradicated by treatment in accordance with the present method. These means can be used separately, or in combination, by the practitioner as suits the needs of an individual human subject.

Optionally, treating further includes administering to the human subject an anti-inflammatory cytokine or an agonist thereof, substantially simultaneously with or after at least partially eradicating the bacterial overgrowth of the small intestine, to accelerate or further improve the symptom(s) of irritable bowel syndrome, fibromyalgia, chronic fatigue syndrome, depression, ADHD, or an autoimmune disease, or Crohn's disease. Useful anti-inflammatory cytokines include human IL4, IL-10, IL-11, or TGF-β, derived from a human source or a transgenic non-human source expressing a human gene. The anti-inflammatory cytokine is preferably injected or infused intravenously or subcutaneously.

Optionally, when the suspected diagnosis is irritable bowel syndrome, fibromyalgia, chronic fatigue syndrome, depression, ADHD, or an autoimmune disease, such as multiple sclerosis or systemic lupus erythematosus, symptoms are improved by administering an antagonist of a pro-inflammatory cytokine or an antibody that specifically binds a pro-inflammatory cytokine. The antagonist or antibody is administered to the human subject substantially simultaneously with or after treatment to at least partially eradicate the bacterial overgrowth. The antagonist or antibody is one that binds to a pro-inflammatory cytokine or antogonizes the activity or receptor binding of a pro-inflammatory cytokine. Pro-inflammatory cytokines include TNF-α, IL-1α, IL-1β, IL-6, IL-8, IL-12, or LIF. The cytokine antagonist or antibody is preferably derived from a human source or is a chimeric protein having a human protein constituent. The cytokine antagonist or antibody is preferably delivered to the human subject by intravenous infusion.

Optionally, the method of treating irritable bowel syndrome, fibromyalgia, chronic fatigue syndrome, depression, attention deficit/hyperactivity disorder, an autoimmune disease, or Crohn's disease, further comprises administering an agent that modifies afferent neural feedback or sensory perception. This is particularly useful when, after at least partial eradication of SIBO, the subject experiences residual symptoms of hyperalgesia related to SIBO or associated with a disorder caused by SIBO, such as IBS, fibromyalgia, or Crohn's disease. Agents that modify afferent neural feedback or sensory perception include 5-HT receptor antagonists, such as ondansetron and alosetron; opiate agonists, such as fedotozine; peppermint oil; cisapride; a dopamine antagonist, such as domperidone; an antidepressant agent; an anxiolytic agent; or a combination of any of these. Useful antidepressant agents include tricyclic antidepressants, such as amitriptyline (Elavil); tetracyclic antidepressants, such as maprotiline; serotonin re-uptake inhibitors, such as fluoxetine (Prozac) or sertraline (Zoloft); monoamine oxidase inhibitors, such as phenelzine; and miscellaneous antidepressants, such as trazodone, venlafaxine, mirtazapine, nefazodone, or bupropion (Wellbutrin). Typically, useful antidepressant agents are available in hydrochloride, sulfated, or other conjugated forms, and all of these conjugated forms are included among the useful antidepressant agents. Useful anxiolytic (anti-anxiety) agents include benzodiazepine compounds, such as Librium, Atavin, Xanax, Valium, Tranxene, and Serax, or other anxiolytic agents such as Paxil.

Representative methods of administering include giving, providing, feeding or force-feeding, dispensing, inserting, injecting, infusing, prescribing, furnishing, treating with, taking, swallowing, eating or applying.

Eradication of the bacterial overgrowth is determined by detection methods described above, particularly in comparison with recorded results from pre-treatment detection. After at least partially eradicating the bacterial overgrowth, in accordance with the present method, the symptom(s) of irritable bowel syndrome, fibromyalgia, chronic fatigue syndrome, depression, ADHD, an autoimmune disease, or Crohn's disease are improved. Improvement in a symptom(s) is typically determined by self-reporting by the human subject, for example by VAS scoring or other questionnaire. Improvement in academic, professional, or social functioning, e.g., in cases of ADHD or depression can also be reported by others or can be observed by the clinician. Improvement (increase) in pain threshold, e.g., in subjects diagnosed with fibromyalgia, can be measured digitally, for example, by tender point count, or mechanically, for example, by dolorimetry. (F. Wolfe et al., Aspects of Fibromyalgia in the General Population: Sex, Pain Threshold, and Fibromyalgia Symptoms, J. Rheumatol. 22:151–56 [1995]).

Improvement in visceral hypersensitivity or hyperalgesia can be measured by balloon distension of the gut, for example, by using an electronic barostat. (B. D. Nabiloff et al., Evidence for two distinct perceptual alterations in irritable bowel syndrome, Gut 41:505–12 11997]). Some improvement(s) in symptoms, for example systemic lupus erythematosus symptoms, such as rashes, photosensitivity, oral ulcers, arthritis, serositis, or improvements in the condition of blood, kidney or nervous system, can be determined by clinical observation and measurement.

The present invention also relates to a kit for the diagnosis and treatment of irritable bowel syndrome, fibromyalgia, chronic fatigue syndrome, depression, ADHD, an autoimmune disease, or Crohn's disease. The kit is a ready assemblage of materials for facilitating the detection and at least partial eradication of small intestinal bacterial overgrowth. The kit includes at least one, and most preferably multiple, air-tight breath sampling container(s), such as a bag, cylinder, or bottle, and at least one pre-measured amount of a substrate, such as lactulose (e.g., 10–20 g units) or glucose (e.g., 75–80 g units), for measuring breath hydrogen and/or methane before and/or after a treatment to at least partially eradicate SIBO. Alternatively, the kit contains pre-measured amount(s) of isotope-labeled substrate as described above. The present kit also contains instructions for a user in how to use the kit to effectively corroborate a suspected diagnosis of irritable bowel syndrome, fibromyalgia, chronic fatigue syndrome, depression, ADHD, an autoimmune disease, or Crohn's disease, in accordance with the present diagnostic method, and how to treat the underlying cause of any of these conditions by at least partially eradicating SIBO.

Optionally, the kit also contains components useful for at least partially eradicating SIBO, for example, unitized amounts of an antimicrobial agent, such as neomycin, metronidazole, teicoplanin, doxycycline, tetracycline, ciprofloxacin, augmentin, cephalexin (e.g., Keflex), penicillin, ampicillin, kanamycin, rifamycin, rifaximin, or vancomycin, or a 4- or 5-aminosalicylate compound, and/or a probiotic agent, such as an inoculum of a species or strain of *Bifidobacterium* or *Lactobacillus*, or a prokinetic agent, such as a peptide or functional analog thereof, macrolide compound, a bile acid, a bile salt, a cholinergic compound, a dopamine antagonist, a nitric oxide altering agent, a 5-HT receptor antagonist, a neuroleptic agent, a kappa agonist, or an antihistamine except ranitidine, famotidine, or nizatidine. Any combination of these can be included in the kit. The kit optionally contains an anti-inflammatory cytokine or an agonist thereof, or an antagonist or antibody effective against a pro-inflammatory cytokine. The kit optionally contains an agent that modifies afferent neural feedback or sensory perception, as described above, for alleviating or improving hyperalgesia related to SIBO or associated with a disorder caused by SIBO, such as IBS, fibromyalgia, or Crohn's disease.

The components assembled in the kits of the present invention are provided to the practitioner stored in any convenient and suitable way that preserves their operability and utility. For example the components can be in dissolved, dehydrated, or lyophilized form; they can be provided at room, refrigerated or frozen temperatures.

The foregoing descriptions for the methods and kits of the present invention are illustrative and by no means exhaustive. The invention will now be described in greater detail by reference to the following non-limiting examples.

EXAMPLES

Example 1
Composition of the Database

Data were assembled from 202 human subjects from the Cedars-Sinai Medical Center GI Motility Program who completed an extensive questionnaire of health history. These patients were all referred for lactulose breath hydrogen testing (LBHT) by more than 30 private gastroenterologists. These patients were selected by their gastroenterologists to undergo breath testing, because they had symptoms compatible with SIBO. However, the questionnaire focused on general risk factors, associated conditions, and symptoms found in these patients and not specifically the incidence of SIBO. After antibiotic therapy, 59 subjects actually returned for a follow up LBHT and a follow-up questionnaire. This likely resulted in an underestimate of responsiveness to treatment, since only those who failed to respond adequately were likely to return to assess eradication of SIBO.

Example 2
Breath Hydrogen Testing

Subjects were tested after an overnight fast. At time zero, each subject swallowed 15 ml of Chronulac formula, delivering 10 g of lactulose; every 5–20 min thereafter, for 2–4 hours, a 50 $cm^3$ end-expiratory breath sample was taken with an airtight sampling bag. Each breath sample was then analyzed for hydrogen content with a gas chromatograph (Quintron Model DP, Quintron Instrument Co., Division of E. F. Brewer Co, Menomonee Falls, Wis. 53051), standardized using a QuinGas standard as instructed by the manufacturer. Hydrogen peaks were plotted before and after an antimicrobial treatment regimen for comparison. The normal range for the second hydrogen peak was 0 to 20 ppm.

Example 3
Diagnosis and Treatment of Irritable Bowel Syndrome

The two hundred-two (202) human subjects were assessed for SIBO with LBHT. Of the 202 subjects in the database, 95 claimed to have been given a diagnosis of IBS. In addition, a symptom questionnaire was used to determine whether these subjects fulfilled Rome criteria for IBS, and four of the subjects failed to meet the Rome criteria. Crohn's disease was present in 14 of the subjects and four had a history of ulcerative colitis. After these 22 subjects were excluded, 73 subjects remained.

Among the 107 subjects who stated that they had not previously been given a diagnosis of IBS, 78 met Rome criteria. After the 21 who had Crohn's disease, five who had ulcerative colitis and one with short bowel transit were excluded, 51 subjects remained. Data gathered from these subjects were pooled with data from the previous 73 subjects with suspected IBS, yielding a total of 124 of the original 202 (61%) subjects with a suspected diagnosis of IBS.

Of the 124, 92 (74%) were positive for SIBO. However, of the 32 subjects meeting the Rome criteria, who were negative for SIBO, 14 had been treated with antibiotics within 3 months prior to LBHT. Therefore, the incidence of SIBO among the 110 untreated subjects was 92 (84%), showing a strong association between a suspected diagnosis of IBS and the presence of SIBO. After neomycin treatment (500 mg twice daily for ten days), 23 of these 92 returned for follow-up testing. On a visual analog scores (VAS), subjects were asked to rate their degree of post-treatment improvement. These 23 subjects reported a 60±31% improvement, although 17 had only partial eradication of SIBO, based on their LBHT results. (FIG. 1).

Figure 2:
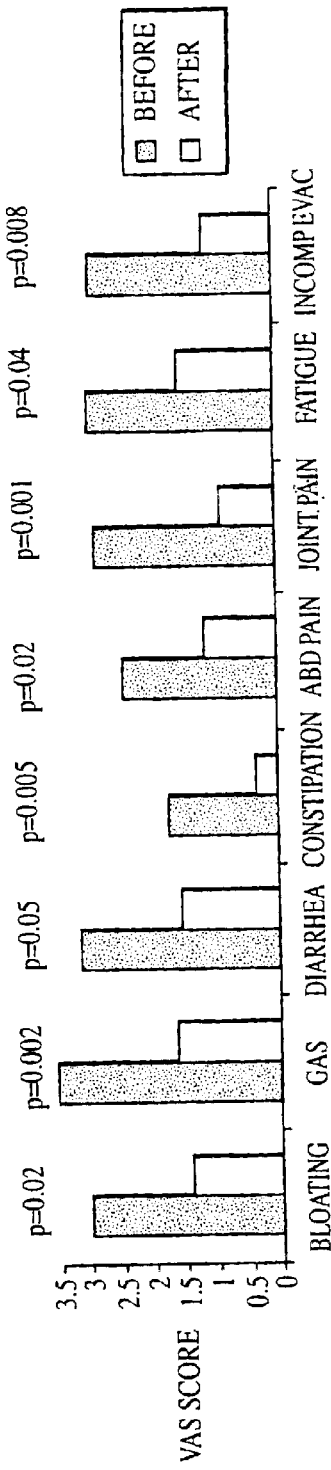
FIG. 2 shows visual analog scores from subjects with IBS and SIBO in a pilot study, before and after antibiotic treatment.

There was a likely selection bias in the database due to the fact that subjects were referred for LBHT, because their physicians suspected they had SIBO. To correct for this bias, a pilot study was also conducted looking at the incidence of bacterial overgrowth in patients with IBS. All patients between the ages of 18 and 65 referred to the Cedars-Sinai GI Motility Program who met Rome criteria for IBS, and who had had a previous upper GI (small bowel) with follow-through (i.e., barium or Gastrograffin imaging analysis) ruling out Crohn's disease and ulcerative colitis, were asked to present to the GI motility laboratory for LBHT. Eight human subjects with a suspected diagnosis of IBS, based on the Rome criteria, were tested for SIBO, using LBHT as described in Example 2. Seven of these patients (87.5%) were found to have SIBO based on hydrogen peaks in a range of 80–250 ppm of hydrogen. Six of the 7 subjects testing positive for SIBO returned approximately 10 days after completion of a 10 day course of neomycin as described above. Neomycin treatment completely eradicated the SIBO in each of the six subjects, based on post-treatment breath hydrogen peaks in the normal range of 0–20 ppm. The six subjects reported an average improvement in their IBS symptoms of 65±28% (Range: 20–100%) on VAS scoring. FIG. 2 shows VAS for the six subjects, based on a scale of 0–5, with 0 implying no pain and 5 the most pain of life-time. It is clear from these results that at least partial eradication of bacterial overgrowth results in an improvement in gastrointestinal symptoms including bloating, gas, diarrhea, abdominal pain, sensation of incomplete evacuation and even constipation, associated with IBS. Additionally, significant extraintestinal symptoms of IBS, such as joint pain and fatigue, were also substantially improved, and the degree of improvement was greater in subjects who had complete eradication of SIBO.

Example 4

Diagnosis and Treatment of Fibromyalgia and Chronic Fatigue Syndrome

Fibromyalgia

Of the 202 patients in the database, 37 (18%) had a suspected diagnosis of fibromyalgia. Of these 37, 28 tested positive for SIBO. However, of the nine who tested negative for SIBO, six had taken antibiotics within the preceding 3 months, and were excluded. Therefore, 28 out of 30 (93%) of subjects with suspected fibromyalgia had SIBO, demonstrating a strong association between a suspected diagnosis of fibromyalgia and the presence of SIBO.

Figure 3:
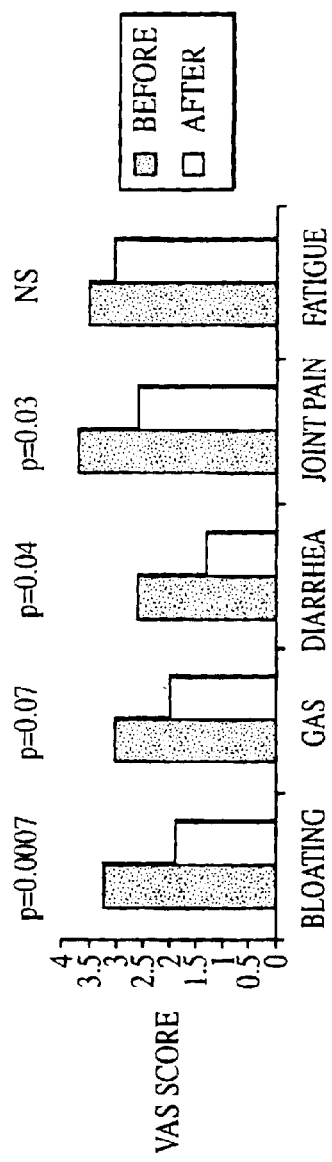
FIG. 3 shows visual analog scores reported by subjects with fibromyalgia and SIBO before and after antibiotic treatment.
Figure 4:
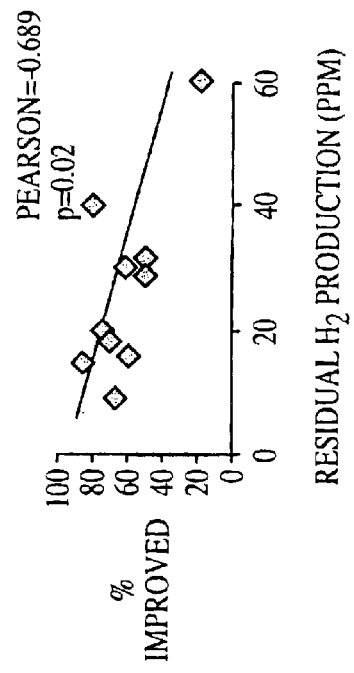
FIG. 4 shows the correlation between the degree of improvement in symptoms and residual breath hydrogen production after antibiotic treatment in subjects with fibromyalgia and SIBO.

After neomycin treatment (500 mg twice daily, 10-day course), ten of these 28 subjects returned, and post-treatment LBHT confirmed that SIBO had been at least partially eradicated. These ten subjects reported a 63±19% overall improvement in their symptoms by VAS scoring. FIG. 3 compares the VAS scores for various symptoms reported by the subjects with a suspected diagnosis of fibromyalgia before and after neomycin treatment. Symptoms included bloating, gas, diarrhea, joint pain and fatigue to treatment. Subjects were asked to identify the symptom most improved. Five subjects reported that pain was the most improved; three subjects reported that the level of fatigue was most improved, and two others reported that their abdominal complaints improved the most. There was a negative correlation between the degree of improvement in the VAS scoring and the amount of residual hydrogen peak seen in LBHT. (Pearson=−0.689, p=0.02; FIG. 4).

Subsequently, forty-six human subjects with FM (ACR criteria) entered a double blind randomized placebo controlled trial. Each subject underwent LBHT, a tender point examination and completed a questionnaire at the initial (baseline) and at every subsequent visit. Subjects were randomized to receive neomycin (500 mg twice daily in liquid form) or a matched placebo, for 10 days. After completion of this treatment, subjects with persistent SIBO received antibiotics (open label) until at least partially eradication was confirmed by LBHT. T-test was used to compare the symptom scores of patients whose SIBO condition was at least partially eradicated with those whose SIBO was not at least partially eradicated.

Forty-two of the 46 FM patients (91.3%) were found to have SIBO. Six out of 20 patients (30%) in the neomycin group achieved complete at least partially eradication in the blinded arm. Only 6 subjects showed no difference in the symptom score before and after the 10 d treatment. Twenty-eight subjects went on to open label treatment with 17 (60.7%) achieving complete at least partially eradication of SIBO. When symptom scores after at least partially eradication of SIBO on double blind or open treatment were compared to baseline, there was significant improvement in Tender Points, Tender Point Score, Hamilton Depression Scale, Fibromyalgia Impact Questionnaire (FIQ), Beck Depression Scale, Health Assessment Questionnaire (HAQ), VAS-Pain, VAS-Memory/Concentration and IBS-Quality of Life (QOL). (Initial data in Table 1). These results confirm that SIBO is associated with fibromyalgia, and that at least partially eradication of SIBO improves symptoms in fibromyalgia.

TABLE 1

Selected Symptom Scores Double Blind Randomized Placebo Controlled Trial with Subjects Diagnosed with Fibromyalgia.

| Observation | Baseline | SIBO eradicated (n = 25) eradicated | P-value | Baseline | SIBO not eradicated (p = 15) eradicated | P-value | eradicated vs. not eradicated P-value |
|---|---|---|---|---|---|---|---|
| Tender Points (TP) | 13.3 ± 2.9 | 10.3 ± 4.2 | 0.01 | 13.6 ± 2.0 | 12.1 ± 4.1 | NS | NS |
| TP Score | 20.3 ± 7.0 | 15.0 ± 9.1 | 0.01 | 23.7 ± 8.0 | 19.9 ± 9.7 | NS | NS |
| FIQ | 66.8 ± 18.2 | 49.5 ± 17.7 | 0.0001 | 72.7 ± 19.9 | 64.1 ± 20.9 | 0.04 | 0.02 |
| VAS-pain (mm) | 80.7 ± 22.7 | 52.4 ± 28.5 | 0.00005 | 87.5 ± 19.6 | 76.2 ± 25.2 | NS | 0.01 |
| HAQ | 42.4 ± 10.5 | 37.7 ± 10.1 | 0.005 | 45.1 ± 11.2 | 43.9 ± 12.1 | NS | NS |

Chronic Fatigue Syndrome

Thirty of 202 subjects in the database (15.9%) had received a diagnosis of chronic fatigue syndrome. Of these 30 subjects, 21 (70%) had SIBO as indicated by LBHT, but four out of the nine without SIBO had recently taken antibiotics. Therefore, the prevalence of SIBO was 21 out of 26 (81%) subjects with a diagnosis of CFS. After treatment with neomycin (500 mg twice daily, 10-day course), nine of the 21 subjects diagnosed with CFS, returned for follow-up LBHT and questionnaire. LBHT showed that all nine subjects experienced at least partially eradication of SIBO, and important symptoms of CFS were substantially improved after treatment. (Table 2).

TABLE 2

VAS scores by CFS patients reporting before and after anti-biotic treatment.

| Symptom | Before Antibiotic | After Antibiotic | P-value |
|---|---|---|---|
| Bloating | 4.3 ± 1.0 | 2.3 ± 1.7 | 0.002 |
| Fatigue | 4.6 ± 1.0 | 3.5 ± 1.4 | 0.02 |

Example 5
Autoimmune Diseases, Depression, and ADHD
SLE

Fifteen of the 202 (7.4%) subjects in the database had been diagnosed with SLE. Of these 15 subjects, 13 (87%) had bacterial overgrowth, as indicated by LBHT. Four of the 15 subjects with SLE returned for follow-up LBHT and questionnaire after treatment with neomycin (500 mg twice daily for 10 days). LBHT results for these four were negative for SIBO, and other significant symptoms were significantly improved after treatment. (Table 3).

TABLE 3

VAS scores by SLE patients reporting before and after anti-biotic treatment.

| Symptom | Before Antibiotic | After Antibiotic | P-value |
|---|---|---|---|
| Bloating | 3.0 ± 2.0 | 1.3 ± 1.3 | 0.1 |
| Joint Pains | 2.5 ± 1.5 | 0.5 ± 0.6 | 0.04 |
| Gas | 3.3 ± 1.7 | 1.9 ± 1.7 | 0.3 |
| Fatigue | 4.6 ± 1.0 | 3.5 ± 1.4 | 0.3 |

Multiple Sclerosis

A 22-year-old female who presented with a history of multiple sclerosis symptoms and with plaques demonstrated on MRI imaging. A suspected diagnosis of multiple sclerosis had been made by a neurologist was based on various neuropathies of the peripheral nervous system, including numbness, tingling, and weakness in the lower extremities, but this subject also had associated bloating, gas, distension and alteration in bowel habits. The subject also complained of a significant fatigue and nausea. The subject underwent LBHT, which detected SIBO. She was subsequently treated with neomycin (500 mg twice daily for 10 days), which at least partially eradicated the bacterial overgrowth. This was followed by complete resolution of her nausea, fatigue, bloating, gas distension and alteration in bowel habits. In addition, the subject showed dramatic improvement and resolution of her neuropathies. She no longer had numbness or tingling in the hands or feet and was functioning quite well. Approximately 6–8 weeks after this initial response, the patient had a relapse of her symptoms, including bloating, gas, distension and neuropathy. She had a repeat LBHT that confirmed a recurrence of SIBO. Upon re-treatment with neomycin (500 mg twice daily for 10 days), she once again experienced complete resolution of her symptoms.

Depression

A 73-year-old female presented with bloating, gas, abdominal distention, and cramping for a period of 3 years prior to LBHT. Symptoms of depression first appeared concurrently with the first appearance of bowel symptoms, and were serious enough that psychiatric hospitalization had been considered by her attending psychiatrist. The subject reported feeling very depressed and was convinced that life was not worth living. The subject's LBHT indicated the presence of a SIBO condition. After treatment with neomycin (500 mg twice daily for 10 days), the subject stated that she felt "100% better." She reported that her depression was completely resolved and that her energy was back to normal. In addition, her bowel symptoms were also completely improved. The subject had been prescribed eight different anti-depressant medications, all of which were discontinued as a result of her improvement.

ADHD

A 13 year-old female was brought in by her mother with a suspected diagnosis of attention deficit/hyperactivity disorder (AD type), made by a pediatrician. Concurrently, she also had significant bloating, gas and some alteration in bowel habits. She had initially been referred for diagnosis by her teachers and school counselors, because she had been having difficulty performing in school for the previous two to three years, after having previously been a very good student. Prior to the detection of SIBO, the subject had been treated with multiple pharmacologic agents for depression, including amitryptiline, with no noticeable improvement in her symptoms.

The subject underwent LBHT that demonstrated the presence of SIBO. The subject was treated with neomycin (500 mg twice daily for 10 days) and after complete at least partially eradication of the bacterial overgrowth, she had resolution of her bowel symptoms. Additionally, she started to get "A" averages in school again after being in the "C" range. She was able to concentrate better, and her teachers noticed a difference in her focus and attitude. Approximately two months later the subject had a relapse in her attention problem which was concurrent with a recurrence of the bacterial overgrowth, as detected by LBHT. After repeat treatment with neomycin (500 mg twice daily for 10 days), the subject again responded with improved concentration and resolution of bowel symptoms.

Example 6
Diagnosis and Treatment of Crohn's Disease

Of the 202 subjects in the database, 39 (19%) had a suspected diagnosis of Crohn's disease. Of these 39, eight demonstrated short bowel transit and one subject produced neither hydrogen nor methane in LBHT; these nine were excluded. Of the 30 remaining subjects, 22 had SIBO. However, of the eight subjects who had a negative LBHT result, five had been treated with antibiotics within the preceding 3 months. If these subjects are excluded, 22 out of 25 (88%) subjects with a suspected diagnosis of Crohn's disease had SIBO, which shows a strong association between a suspected diagnosis of Crohn's disease and the presence of SIBO.

Figure 5:
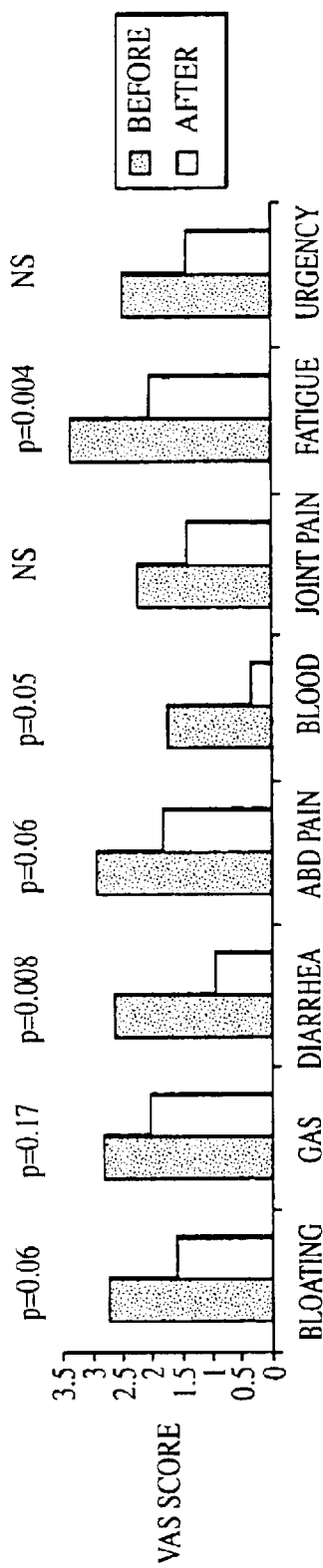
FIG. 5 shows visual analog scores reported by subjects with Crohn's disease and SIBO before and after antibiotic treatment.

Of the 22 patients testing positive for the presence of SIBO, nine returned after neomycin treatment (10-day course of 500 mg twice/daily) for LBHT, which showed at least partially eradication of SIBO. These nine patients reported a 57±32% (n=8 because one patient failed to report percent improvement) overall improvement in their symptoms by VAS. If these subjects remained positive after antibiotic treatment with neomycin, metronidazole (Flagyl®), or ciprofloxacin, their improvement was only 20±0% as opposed to 69±27% if the breath test was negative (p<0.05). FIG. 5 shows a dramatic improvement in the patients symptoms after treatment. There was an especially notable reduction in bloody stools, diarrhea and fatigue.

Figure 6:
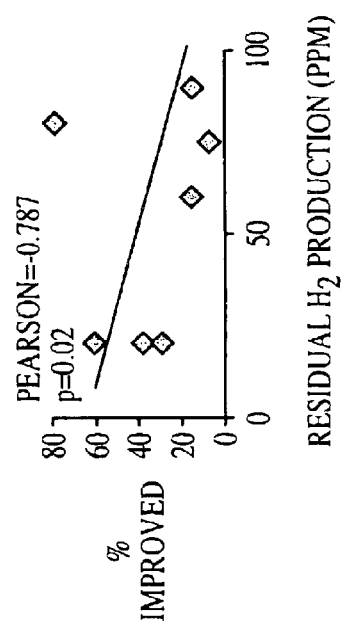
FIG. 6 shows the correlation between degree of improvement in symptoms and residual breath hydrogen production after antibiotic treatment in subjects with Crohn's disease.

As with the subjects with fibromyalgia, there was a negative correlation between the degree of improvement in the VAS scoring and the amount of residual hydrogen production (Pearson=−0.787, p=0.02; FIG. 6).

To correct for selection bias, a pilot study was conducted to determine the incidence of SIBO in subjects who had received a suspected diagnosis of Crohn's disease at Cedars-Sinai Medical Center's IBD Center within the preceding three months. Six of these subjects underwent LBHT, of whom five (83%) were positive for SIBO.

Two of the six subjects returned for follow-up after antibiotic therapy (10-day course of neomycin). Post-treatment LBHTs showed that SIBO had been completely at least partially eradicated in both subjects. They reported, respectively, a 60% and 80% overall improvement in their symptoms. This improvement was stated to include substantial reduction in diarrhea, gas and bloating.

Example 7
Response Stratification

There is a stratification in the degree of overgrowth and production of hydrogen among the various diagnostic categories. For example, during the double blind study in the treatment of SIBO in fibromyalgia (Example 4), it was noted that the level of hydrogen production during the LBHT was much higher in this group of subjects as compared to those in subjects in the IBS incidence study described in Example 3. Given that the bacterial load is related to the level of hydrogen production, this implies that the degree of overgrowth is higher in patients with fibromyalgia compared to subjects with IBS.

The stratification of breath hydrogen levels with respect to diagnostic categories is as follows: IBS/Crohn's Disease (40–70 ppm of hydrogen); CFS (50–100 ppm of hydrogen); and FM (100–250 ppm of hydrogen).

Example 8
Intestinal Dysmotility Associated with IBS and FM

Clinical experience showed that SIBO tends to recur after anti-biotic treatment within about 2 months. To demonstrate that a lack of phase III interdigestive motility is responsible for SIBO in subjects with IBS or fibromyalgia, antreduodenal manometry was conducted in human subjects diagnosed with IBS or FM.

Antreduodenal Manometry

PhaseIII interdigestive (fasting) motility was assessed in 15 human subjects. An antreduodenal manometry was performed by placing an 8-channel small bowel manometry catheter (each channel spaced 5 cm apart) into the small bowel using fluoroscopic guidance. After placement of the catheter, manometric recordings were made with an Arndorffer perfusion system with signals collected using Medtronics/Synectics Polygraf and associated Polygram software. Data were assessed for the characteristics of interdigestive motility.

IBS

Phase III interdigestive motility was assessed for a six-hour period in 15 human subjects having a suspected diagnosis of IBS, as defined by Rome Criteria, corroborated by concomitant SIBO. Of these 15 subjects, 13 (86%) had no detectable phase III interdigestive motility during the period of study. One subject (7%) had phase III interdigestive motility of short duration (<3 minutes), and one subject (7%) had normal phase III interdigestive motility.

Fibromyalgia

Phase III interdigestive motility was assessed in seven human subjects having a suspected diagnosis of fibromyalgia corroborated by the presence of SIBO. Of these seven subjects, six (86%) lacked detectable phase III interdigestive motility, and one subject (14%) had motility of less than normal peristaltic amplitude. The duration of study in the patients with fibromyalgia averaged 216±45 minutes in the fasting state.

Example 9
Treatment of IBS with a Prokinetic Agent

Erythromycin, as a motilin agonist, can induce phase III of interdigestive motility. (E.g., M. J. Clark et al., Erythromycin derivatives ABT229 and GM 611 act on motilin receptors in the rabbit duodenum, Clin. Exp. Pharmacol. Physiol. 26(3):242–45 [1999]). Therefore, two subjects with recurrent IBS symptoms received prokinetic treatment with erythromycin.

The two subjects were a 55-year-old female and a 43-year-old female, both diagnosed with IBS. SIBO was detected in these subjects by LBHT. Antibiotic treatment of the SIBO resulted in greater than 90% improvement in symptoms. However, IBS symptoms recurred three to four weeks later, concurrent with a return of the SIBO condition. Subsequent courses of antibiotic treatment resulted in a similar pattern of improvement followed by a rapid recurrence of IBS symptoms in both subjects. Antreduodenal manometry was performed, demonstrating a lack of phase III of interdigestive motility, and erythromycin (50 mg daily) was prescribed to the subjects. The two subjects subsequently remained free of IBS symptoms and SIBO for at least 18 months and six months, respectively.

These results demonstrate the effectiveness of prokinetic treatment with erythromycin in preventing the recurrence of SIBO and IBS symptoms in subjects diagnosed with IBS.

Example 10
Treatment of SIBO-related Hyperalgesia

An adult male subject with a suspected diagnosis of IBS was found to have SIBO, as detected by LBHT. Anorectal manometry revealed rectal hypersensitivity in this subject. After eradication of his SIBO condition with antibiotic treatment, a repeat anorectal manometry showed that his rectal hyperalgesia had resolved.

Two adult female subjects with IBS required additional pharmacologic manipulations to treat their SIBO-related hyperalgesia. In the first case, SIBO was eradicated by antibiotic treatment. However, the subject complained of persistent feelings of rectal distension, consistent with residual hyperalgesia related to SIBO. The subjected was then administered Colpermin (peppermint oil) capsules and Elavil (5 mg taken at night) that alleviated her SIBO-related hyperalgesic symptoms, presumably by reducing intestinal wall tension and decreasing mechanoreceptor activation.

The second female subject with a diagnosis of IBS was also found to have SIBO, as detected by LBHT. Her SIBO was eradicated by a combined treatment with antibiotic, intestinal lavage with Go-Lytely, and cisapride (10 mg tid) to increase her abnormally low phase III interdigestive motility. After eradication of SIBO, this subject similarly complained of persistent SIBO-related hyperalgesic symptoms of the bowel. Administration of Colpermin (peppermint oil) then successfully alleviated the hyperalgesia, presumably by reducing the mechanoreceptor feedback for rectal distension.

The foregoing examples being illustrative but not an exhaustive description of the embodiments of the present invention, the following claims are presented.

We claim:

1. A method of treating irritable bowel syndrome comprising:
    detecting the presence of small intestinal bacterial overgrowth in a human subject having at least one symptom associated with a suspected diagnosis of irritable bowel syndrome; and
    at least partially eradicating the small intestinal bacterial overgrowth to treat the irritable bowel syndrome.

2. The method of claim 1, wherein at least partially eradicating the small intestinal bacterial overgrowth further comprises administering an antimicrobial agent.

3. The method of claim 1, wherein at least partially eradicating the small intestinal bacterial overgrowth further comprises administering an antibiotic.

4. The method of claim 2, wherein the antimicrobial agent is selected from the group consisting of neomycin, metronidazole, teicoplanin, ciprofloxacin, doxycycline, tetracycline, augmentin, cephalexin, penicillin, ampicillin, kanamycin, rifamycin, vancomycin, rifaximin, and combinations thereof.

5. The method of claim 3, wherein the antibiotic is rifaximin.

6. The method of claim 1, wherein at least partially eradicating the small intestinal bacterial overgrowth further comprises administering a probiotic agent.

7. The method of claim 6, wherein the probiotic agent is at least one species or strain of bacterium selected from the group consisting of *Bifidobacterium, Lactobacillus* and combinations thereof.

8. The method of claim 1, wherein at least partially eradicating the small intestinal bacterial overgrowth further comprises administering a prokinetic agent.

9. The method of claim 8, wherein the prokinetic agent is selected from the group consisting of a peptide, motilin, a macrolide compound, a bile acid, a bile salt, a cholinergic compound, a dopamine antagonist, a nitric oxide altering agent, a 5-HT receptor antagonist, a neuroleptic agent, a kappa agonist, an antihistamine, cisapride, metoclopramide, domperidone, bethanechol, erythromycin, azithromycin, nomega-nitro-L-arginine methylester, N-monomethyl-L-arginine, ondansetron, alosetron, promethazine, meclizine, prochlorperazine, chlorpromazine, haloperidol, fedotozine and combinations thereof.

10. The method of claim 8, wherein the prokinetic agent is motilin.

11. A method of treating fibromyalgia comprising:
    detecting the presence of small intestinal bacterial overgrowth in a human subject having at least one symptom associated with a suspected diagnosis of fibromyalgia; and
    at least partially eradicating the small intestinal bacterial overgrowth to treat the fibromyalgia.

12. The method of claim 11, wherein at least partially eradicating the small intestinal bacterial overgrowth further comprises administering an antimicrobial agent.

13. The method of claim 11 wherein at least partially eradicating the small intestinal bacterial overgrowth further comprises administering an antibiotic.

14. The method of claim 12, wherein the antimicrobial agent is selected from the group consisting of neomycin, metronidazole, teicoplanin, ciprofloxacin, doxycycline, tetracycline, augmentin, cephalexin, penicillin, ampicillin, kanamycin, rifamycin, vancomycin, rifaximin, and combinations thereof.

15. The method of claim 13, wherein the antibiotic is rifaximin.

16. The method of claim 11, wherein at least partially eradicating the small intestinal bacterial overgrowth further comprises administering a probiotic agent.

17. The method of claim 16, wherein the probiotic agent is at least one species or strain of bacterium selected from the group consisting of *Bifidobacterium, Lactobacillus* and combinations thereof.

18. The method of claim 11, wherein at least partially eradicating the small intestinal bacterial overgrowth further comprises administering a prokinetic agent.

19. The method of claim 18, wherein the prokinetic agent is selected from the group consisting of a peptide, motilin, a macrolide compound, a bile acid, a bile salt, a cholinergic compound, a dopamine antagonist, a nitric oxide altering agent, a 5-HT receptor antagonist, a neuroleptic agent, a kappa agonist, an antihistamine, cisapride, metoclopramide, domperidone, bethanechol, erythromycin, azithromycin, nomega-nitro-L-arginine methylester, N-monomethyl-L-arginine, ondansetron, alosetron, promethazine, meclizine, prochlorperazine, chlorpromazine, haloperidol, fedotozine and combinations thereof.

20. The method of claim 18, wherein the prokinetic agent is motilin.

21. A method of treating Crohn's disease comprising:
    detecting the presence of small intestinal bacterial overgrowth in a human subject having at least one symptom associated with a suspected diagnosis of Crohn's disease; and
    at least partially eradicating the small intestinal bacterial overgrowth to treat the Crohn's disease.

22. The method of claim 21, wherein at least partially eradicating the small intestinal bacterial overgrowth further comprises administering an antimicrobial agent.

23. The method of claim 21, wherein at least partially eradicating the small intestinal bacterial overgrowth further comprises administering an antibiotic.

24. The method of claim 22, wherein the antimicrobial agent is selected from the group consisting of neomycin, metronidazole, teicoplanin, ciprofloxacin, doxycycline, tetracycline, augmentin, cephalexin, penicillin, ampicillin, kanamycin, rifamycin, vancomycin, rifaximin, and combinations thereof.

25. The method of claim 23, wherein the antibiotic is rifaximin.

26. The method of claim 21, wherein at least partially eradicating the small intestinal bacterial overgrowth further comprises administering a probiotic agent.

27. The method of claim 26, wherein the probiotic agent is at least one species or strain of bacterium selected from the group consisting of *Bifidobacterium, Lactobacillus* and combinations thereof.

28. The method of claim 21, wherein at least partially eradicating the small intestinal bacterial overgrowth further comprises administering a prokinetic agent.

29. The method of claim 28, wherein the prokinetic agent is selected from the group consisting of a peptide, motilin, a macrolide compound, a bile acid, a bile salt, a cholinergic compound, a dopamine antagonist, a nitric oxide altering agent, a 5-HT receptor antagonist, a neuroleptic agent, a kappa agonist, an antihistamine, cisapride, metoclopramide, domperidone, bethanechol, erythromycin, azithromycin, nomega-nitro-L-arginine methylester, N-monomethyl-L-arginine, ondansetron, alosetron, promethazine, meclizine, prochlorperazine, chlorpromazine, haloperidol, fedotozine and combinations thereof.

30. The method of claim 28, wherein the prokinetic agent is motilin.

31. A method of treating a condition modulated by small intestinal bacterial overgrowth comprising:
    detecting the presence of small intestinal bacterial overgrowth in a human subject having at least one symptom associated with a suspected diagnosis of the condition; and
    at least partially eradicating the small intestinal bacterial overgrowth to treat the condition,
    wherein the condition is selected from the group consisting of chronic fatigue syndrome, depression, attention deficit/hyperactivity disorder and multiple sclerosis.

* * * * *